United States Patent
Szolcsányi et al.

(10) Patent No.: US 10,344,032 B2
(45) Date of Patent: Jul. 9, 2019

(54) AGENTS FOR TREATING NEUROGENIC INFLAMMATION AND NEUROPATHIC HYPERALGESIA RELATED DISORDERS

(71) Applicants: PÉCSI TUDOMÁNYEGYETEM, Pécs (HU); VICHEM CHEMIE KUTATÖ KFT., Budapest (HU); Csaba Kéri, Budapest (HU)

(72) Inventors: János Szolcsányi, Pécs (HU); Erika Pintér, Pécs (HU); Zsuzsanna Helyes, Pécs (HU); Éva Szöke, Kozármisleny (HU); Frigyes Wáczek, Budapest (HU); László Örfi, Budapest (HU); György Kéri, Budapest (HU); Tamás Szüts, Budapest (HU)

(73) Assignee: Pécsi Tudományegyetem, Pécs (HU)

( * ) Notice: Subject to any disclaimer, the term of this patent is extended or adjusted under 35 U.S.C. 154(b) by 0 days.

(21) Appl. No.: 15/511,697

(22) PCT Filed: Oct. 28, 2014

(86) PCT No.: PCT/HU2014/000097
§ 371 (c)(1),
(2) Date: Mar. 16, 2017

(87) PCT Pub. No.: WO2016/042349
PCT Pub. Date: Mar. 24, 2016

(65) Prior Publication Data
US 2017/0260187 A1    Sep. 14, 2017

Related U.S. Application Data

(60) Provisional application No. 62/058,752, filed on Oct. 2, 2014.

(30) Foreign Application Priority Data

Sep. 17, 2014   (HU) .................................. P1400432

(51) Int. Cl.
| | |
|---|---|
| C07D 487/04 | (2006.01) |
| C07D 487/00 | (2006.01) |
| A61K 31/519 | (2006.01) |
| A61P 29/00 | (2006.01) |
| A61P 25/02 | (2006.01) |

(52) U.S. Cl.
CPC .................................. *C07D 487/00* (2013.01)

(58) Field of Classification Search
CPC ........................... C07D 487/04; A61K 31/519
See application file for complete search history.

(56) References Cited

U.S. PATENT DOCUMENTS

| 6,686,366 B1 | 2/2004 | Castelhano et al. |
| 6,765,008 B1 | 7/2004 | Chen |
| 2004/0242595 A1 | 12/2004 | Eggenweiler et al. |
| 2008/0214583 A1 | 9/2008 | Szolcsanyi et al. |

OTHER PUBLICATIONS

Database Chemcats, Chemical Abstract Service, Columbus, Ohio, 2014, Database Accession Nos. 1602274006 and 1191383336, Registry No. 879578-78-6.
Marquet et al: "Sur une nouvelle série d'analogues puriques à action antimitotique: relations structure-activité", Chimie Therapeutique, 1971, vol. 6, pp. 427-438.

*Primary Examiner* — Susanna Moore
(74) *Attorney, Agent, or Firm* — Jason D. Voight

(57) ABSTRACT

The present invention relates to 4-phenetylamino-7H-pyrrolo[2,3-d]pyrimidine derivatives of the and solvates, hydrates and pharmaceutically acceptable salts thereof, processes for manufacturing of them, the use of them, as well as pharmaceutical compositions containing at least one of them as pharmaceutically active agent(s) together with pharmaceutically acceptable carrier, excipient and/or diluents, especially for the prevention and/or treatment of acute neurogenic inflammation and/or neuropathic hyperalgesia. Said 4-phenetylamino-7H-pyrrolo[2,3-d]pyrimidine compounds have been identified as new drug candidates for the prevention and/or treatment of acute neurogenic inflammation and/or neuropathic hyperalgesia.

15 Claims, 5 Drawing Sheets

US 10,344,032 B2

AGENTS FOR TREATING NEUROGENIC INFLAMMATION AND NEUROPATHIC HYPERALGESIA RELATED DISORDERS

This is the national stage of International Application PCT/HU2014/000097, filed Oct. 28, 2014.

FIELD OF THE INVENTION

The present invention relates to 4-phenetylamino-7H-pyrrolo[2,3-d]pyrimidine derivatives of the general formula (I) and solvates, hydrates and pharmaceutically acceptable salts thereof, processes for manufacturing of them, the use of them, as well as pharmaceutical compositions containing at least one of them as pharmaceutically active agent(s) together with pharmaceutically acceptable carrier, excipient and/or diluents, especially for the prevention and/or treatment of acute neurogenic inflammation and/or neuropathic hyperalgesia. Said 4-phenetylamino-7H-pyrrolo[2,3-d]pyrimidine compounds have been identified as new drug candidates for the prevention and/or treatment of acute neurogenic inflammation and/or neuropathic hyperalgesia.

BACKGROUND OF THE INVENTION

Neurogenic inflammation and neuropathic pain are mediated by the mechanical damage of peptidergic sensory nerves (in case of traumatic neuropathy) or chemical activation of peptidergic sensory nerves (in case of neurogenic inflammation), resulting in pathological activation and dysfunctions of peptidergic sensory nerves. The undesired activation and dysfunction is implicated in severe hyperalgesia (the threshold of a painful stimulus causing nocifensive behaviour remarkably decreases) and allodynia (non-painful stimulus becomes painful and induces nocifensive behaviour).

Traumatic neuropathy induced by mechanical nerve damage (e.g. suffered in accidents, bone fractures or operations) is mediated by complex mechanisms at the levels of both the peripheral and central nerve endings in the respective innervated region, spinal dorsal horn and other pain-related brain regions. Neuropathies caused by traumatic events (mechanical damage-induced axonopathies) affect only one or a few anatomical structures (mononeuropathy) and result in pathological activation and dysfunctions of peptidergic sensory nerves. In these cases, neuropathic pain is caused by different mechanisms compared to metabolic or toxic polyneuropathies, such as abnormal crosstalk between sensory and sympathetic nerves, changes in the expression of different ion channels, marked glial cell activation etc., and mediated by different signaling molecules than in diabetic neuropathy (Banoliel R et al., Oral Dis., 2012, 18(4):317-32; Aley K O. and Levine J D, Neuroscience., 2002, 111(2):389-97). There are also differences in the therapy of diabetic and traumatic neuropathies. Causal pharmacotherapeutic agents (alpha-lipoic acid, benfotiamine) exerting an action based on the pathophysiological mechanism of the disease is only available in diabetic, but not in traumatic neuropathy (Miranda-Massari J R et al., Curr Clin Pharmacol., 2011, 6(4):260-73). Drugs used as symptomatic therapy for diabetic neuropathic pain include antidepressants, anticonvulsants, opioids and some other groups (e.g.: topical lidocain, capsaicin). Their effectiveness is well documented by clinical evidence-based data in painful polyneuropathies (such as diabetic) and postherpetic neuralgia, but not in traumatic neuropathy. Additionally, these drugs do not treat the cause of neuropathic pain and are not effective in a large proportion of patients (Finnerup et al., Pain., 2010, 150(3):573-81).

Peripheral and central sensitization mechanisms play important roles in the development of severe persistent chronic pain induced by mechanical nerve damage, which is not effectively treated by the conventional analgesics. Therefore, intensive traumatic neuropathic pain is a clinically challenging problem, since opioids and cyclo-oxygenase (COX) inhibitor non-steroidal anti-inflammatory agents (NSAIDs) are not potent in these conditions. Adjuvant analgesics, such as certain antiepileptics and antidepressants acting in the central nervous system (CNS) by inhibiting the ascending pain pathway and/or activating the descending inhibitory pathway can be used in some patients, but they cannot be regarded as optimal therapeutic solutions for the problems due to severe acute side effects (cardiovasular, CNS) and/or chronic toxicity.

Furthermore, neurogenic inflammation (vasodilatation, plasma protein extravasation, inflammatory cell activation) induced by the stimulation of peptidergic sensory nerves and the released pro-inflammatory sensory neuropeptides (substance P, calcitonin gene-related peptide) play a very important role in a variety of different acute and chronic inflammatory painful diseases (Chiu et al., Nat. Neurosci., 2013, 15(8):1063-7), although it is not the exclusive mechanism. This is a basically different inflammatory mechanism compared to immune cell-mediated processes, it is often the very early initiation step even in chronic diseases, which triggers and then remarkably augments further cellular pathways. The neurogenic inflammatory component is not inhibited by the conventional anti-inflammatory drugs (COX inhibitors), and glucocorticoids are only moderately effective in extremely high doses in which they exert very many severe side-effects that limit their clinical applications. Therefore, it is particularly important to identify novel therapeutical mechanisms and targets to inhibit neurogenic inflammatory pain. This could substantially help the treatment of chronic inflammatory disorders providing long-term therapeutical benefits for a great patient population.

Subject molecules of the present invention are new and have been identified as active agents in neurogenic inflammation and neuropathic hyperalgesia models. Although compound (a) has very similar structure, it was published as antimicotic substance (Chimica Therapeutica vol 6. (1971) 427-437) and was found totally inactive in the analgesic and anti-inflammatory models, which are shown within the examples of the present invention. This finding supports our "theory of methoxy groups". Dimethoxy is not allowed in general formula (I) of the present invention on R1 phenyl and monomethoxy is more tolerable on R4 phenyl compared with dimethoxy substitution in analgesic and anti-inflammatory activity point of view.

Related N-benzylidene-N'-(7H-pyrrolo[2,3-d]pyrimidin-4-yl)-hydrazine derivates in WO2005105804 patent have analgesic and anti-inflammatory effect. These anti-inflammatory agents of formula (b) contain hidrazone moiety, controversially to the substances of the present invention, which have methylene-amino group at the same position. Surprisingly this replacement of hidrazone moiety with methylene-amino one has not ruined the analgesic and anti-inflammatory activity of the invented substances.

(a)
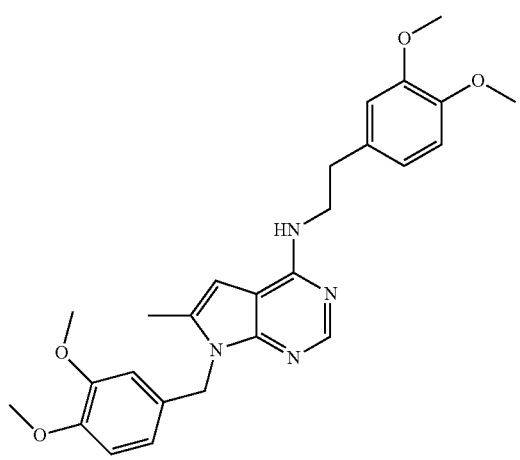

(b)
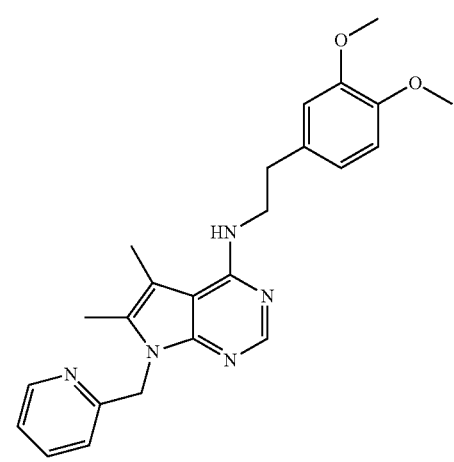

(a1)
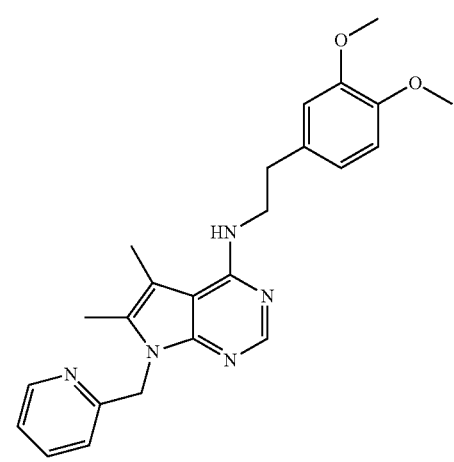

(a2)
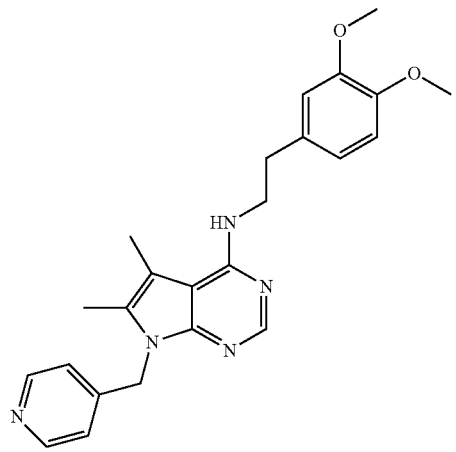

(a3)
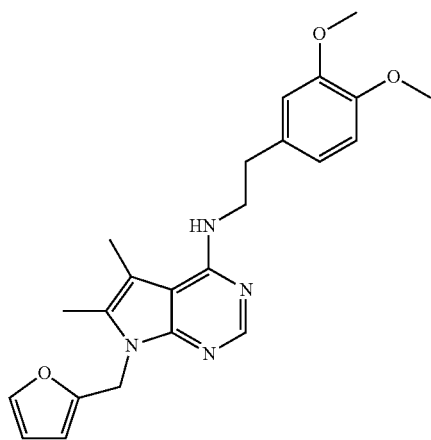

(a4)
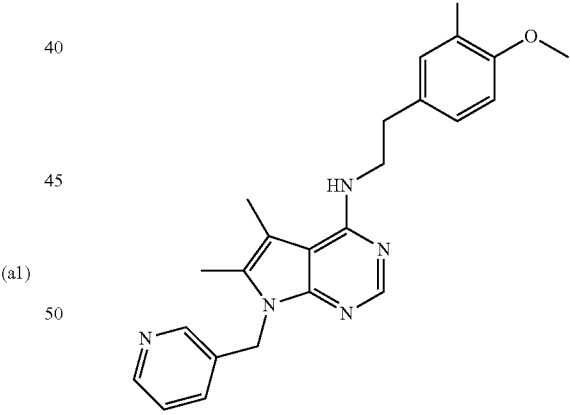

Further dimethoxy-4-phenetylamino-7H-pyrrolo[2,3-d] pyrimidine derivatives (a1) to (a4) are disclosed under CAS Registry Number 951981-71-8, 929850-23-7, 906261-62-9 and 903852-84-6, respectively. Although there is no information relating to their effect, if any, these compounds overlap with the general formula (I) (see below), therefore they are excluded from the claimed scope.

WO 94/13676 A1 discloses a general formula which encompasses compounds having similar structure to that of the claimed ones but there is no methylene moiety between the N of the 7H-pyrrolo[2,3-d]pyrimidin and the aryl (R1 in the present general formula I). The claimed compounds are corticotropin releasing factor antagonists and they are used for treating CRF induced illnesses or inflammatory diseases such as arthritis, asthma and allergies. Closest possible compounds embraced by the scope are not disclosed by examples, moreover, in the examples the moiety corresponding to our R4 in most cases is other than aryl. When R4 is aryl, the moiety linking said aryl to the pyrrolo-pyrimidine comprises N or O. Furthermore; the document does not contain any biological data confirming the claimed pharmaceutical effect.

Structurally similar compounds are disclosed in WO 03/031447 but they are substituted in position 2 of the pyrrolo-pyrimidine ring. Said compounds show a phosphodiesterase V inhibitiory activity and can be used for treatment of diseases of the coronary circulatory system and for treatment and/or therapy of potency disorders.

Compounds having 7H-pyrrolo[2,3-d]pyrimidine backbone and substituents different from that of the present invention as defined below are described in U.S. Pat. No. 6,686,366. The invention relates to compound effective in the treatment of diseases associated with A3 adenosine receptors. Said diseases are respiratory disorder or gastrointestinal disorder, for example diarrhea, asthma, allergic rhinititis and the like. The document thoroughly describes the role of several different substituents which are linked to different position of the pyrrolo-pyrimidine skeleton in the inhibition of said A3 adenosine receptors.

SUMMARY OF THE INVENTION

1. The present invention relates to compounds of the general formula (I) and their solvates, hydrates and pharmaceutically acceptable salts:

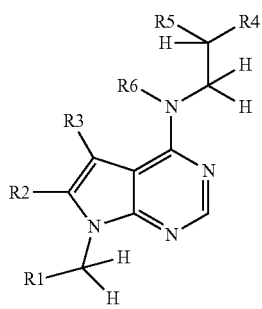

wherein
R1 is substituted or unsubstituted aryl (preferably phenyl), substituted or unsubstituted heteroaryl, RaRbN—(C1-4 alkyl), where Ra and Rb are independently from each other C1-4 alkyl;
R2, R3 are independently from each other hydrogen or C1-4 alkyl;
R4 is aryl (preferably phenyl) optionally substituted with 1 to 3 substituent(s) selected independently from each other from the group of halogen, hydroxyl, alkoxy, —NH$_2$, —NRcRd, where Rc and Rd are independently from each other C1-4 alkyl, isoindole-1,3-dione-2-yl, —NHCOR7, —NHSO$_2$R7 and —NHCONHR7;
R5 is hydrogen or hydroxyl;
R6 is hydrogen or C1-4 alkyl;
R7 is C1-4 alkyl, C1-4 alkyl-CO—C1-4 alkoxy, —NReRf, where Re and Rf are independently from each other C1-4 alkyl, or aryl (preferably phenyl) optionally substituted with 1 to 3 substituent(s) selected independently from each other from the group of halogen, C1-4 alkyl, C1-4 alkoxy and trifluoromethyl
with the proviso that R1 is other than unsubstituted pyridinyl, unsubstituted furanyl or dimethoxyphenyl when R4 is dimethoxyphenyl, R2 is methyl, R3 is hydrogen or methyl, and R5 and R6 are hydrogen.

2. In a further embodiment the invention relates to compounds according to above point 1, wherein
R1 is substituted or unsubstituted phenyl, furanyl, pyridinyl, thienyl, pyrimidinyl or piperazinyl, RaRbN—(C1-3 alkyl), where Ra and Rb are independently from each other C1-3 alkyl;
R2, R3 are independently from each other hydrogen or C1-3 alkyl;
R4 is phenyl optionally substituted with 1 to 3 substituent(s) selected independently from each other from the group of halogen, hydroxyl, alkoxy, —NH$_2$, —NRcRd, where Rc and Rd are independently from each other C1-3 alkyl, isoindole-1,3-dione-2-yl, —NHCOR7, —NHSO$_2$R7 and —NHCONHR7;
R5 is hydrogen or hydroxyl;
R6 is hydrogen or C1-3 alkyl;
R7 is C1-3 alkyl, C1-3 alkyl-CO—C1-3 alkoxy, —NReRf, where Re and Rf are independently from each other C1-3 alkyl, or phenyl optionally substituted with 1 to 3 substituent(s) selected independently from each other from the group of halogen, C1-3 alkyl, C1-3 alkoxy and trifluoromethyl.

3. In a further embodiment the invention relates to compounds according to above point 1 or 2, wherein
R1 is substituted or unsubstituted phenyl, furanyl, pyridinyl, thienyl, pyrimidinyl or piperazinyl, RaRbN—(C1-2 alkyl), where Ra and Rb are independently from each other C1-2 alkyl;
R2, R3 are independently from each other hydrogen or C1-2 alkyl;
R4 is phenyl optionally substituted with 1 to 2 substituent(s) selected independently from each other from the group of halogen, hydroxyl, alkoxy, —NH$_2$, —NRcRd, where Rc and Rd are independently from each other C1-2 alkyl, isoindole-1,3-dione-2-yl, —NHCOR7, —NHSO$_2$R7 and —NHCONHR7;
R5 is hydrogen or hydroxyl;
R6 is hydrogen or C1-2 alkyl;
R7 is C1-2 alkyl, C1-2 alkyl-CO—C1-2 alkoxy, —NReRf, where Re and Rf are independently from each other C1-2 alkyl, or phenyl optionally substituted with 1 to 2 substituent(s) selected independently from each other from the group of halogen, C1-2 alkyl, C1-2 alkoxy and trifluoromethyl.

4. In a further embodiment the invention relates to compounds according to any of above points 1 to 3, wherein
R1 is substituted or unsubstituted phenyl, furanyl or pyridinyl, or Me$_2$N-ethyl;
R2, R3 are independently from each other hydrogen or methyl;
R4 is phenyl optionally substituted with 1 to 2 substituent(s) selected independently from each other from the group of halogen, hydroxyl, methoxy, —NH$_2$, —NMe$_2$, isoindole-1,3-dione-2-yl, —NHCOR7, —NHSO$_2$R7 and —NHCONHR7;
R5 is hydrogen or hydroxyl;
R6 is hydrogen or methyl;
R7 is methyl, ethyl-CO-methoxy, —NEt$_2$, or phenyl optionally substituted with 1 to 2 substituent(s) selected independently from each other from the group of halogen, methyl, methoxy and trifluoromethyl.

5. In a further embodiment the invention relates to compounds according to any of above points 1 to 4, wherein
R1 is unsubstituted phenyl or furan-2-yl, 3-chloro-fenyl, 5-bromo-pyridine-3-yl or Me$_2$N-ethyl;
R2, R3 are independently from each other hydrogen or methyl;
R4 is phenyl optionally substituted with 1 to 2 substituent(s) selected independently from each other from the group of halogen, hydroxyl, methoxy, —NH$_2$, —NMe$_2$, isoindole-1,3-dione-2-yl, —NHCOR7, —NHSO$_2$R7 and —NHCONHR7;
R5 is hydrogen or hydroxyl;
R6 is hydrogen or methyl;
R7 is methyl, ethyl-CO-methoxy, —NEt$_2$, or phenyl optionally substituted with 1 to 2 substituent(s) selected independently from each other from the group of halogen, methyl, methoxy and trifluoromethyl.

6. In a further embodiment the invention relates to compounds according to any of above points 1 to 5, wherein R1 to R3, R5 and R6 are as defined above and
R4 is phenyl, hydroxy-phenyl, amino-phenyl, dimethyl-amino-phenyl, methoxy-phenyl, dimethoxy-phenyl, chloro-phenyl, fluoro-phenyl, phenyl-isoindole-1,3-dione, phenyl-acetamide, phenyl-3-(2,4-difluoro-phenyl)-urea, phenyl-benzamide, phenyl-3-trifluoromethyl-benzamide, phenyl-4-chloro-benzamide, phenyl-1,1-diethyl-urea, phenyl-methanesulfonamide, phenyl-2,4-difluoro-benzenesulfonamide, phenyl-succinamic acid methyl ester or phenyl-3-(3-trifluoromethyl-phenyl)-urea.

7. In a further embodiment the invention relates to compounds selected from the group of
(7-Benzyl-5,6-dimethyl-7H-pyrrolo[2,3-d]pyrimidin-4-yl)-[2-(4-methoxy-phenyl)-ethyl]-amine (ex. 2);
[7-(3-Dimethylamino-propyl)-5,6-dimethyl-7H-pyrrolo[2,3-d]pyrimidin-4-yl]-[2-(4-methoxy-phenyl)-ethyl]-amine (ex. 41);
N-{4-[2-(7-Benzyl-5,6-dimethyl-7H-pyrrolo[2,3-d]pyrimidin-4-ylamino)-ethyl]-phenyl}-acetamide (ex. 3);
N-(4-{2-[7-(3-Dimethylamino-propyl)-5,6-dimethyl-7H-pyrrolo[2,3-d]pyrimidin-4-ylamino]-ethyl}-phenyl)-acetamide (ex. 51);
(7-Benzyl-5,6-dimethyl-7H-pyrrolo[2,3-d]pyrimidin-4-yl)-[2-(3-methoxy-phenyl)-ethyl]-amine (ex. 40);
3-[2-(7-Benzyl-5,6-dimethyl-7H-pyrrolo[2,3-d]pyrimidin-4-ylamino)-ethyl]-phenol (ex. 58);
4-[2-(7-Benzyl-5,6-dimethyl-7H-pyrrolo[2,3-d]pyrimidin-4-ylamino)-ethyl]-phenol (ex. 4);
(7-Benzyl-5,6-dimethyl-7H-pyrrolo[2,3-d]pyrimidin-4-yl)-[2-(3-chloro-phenyl)-ethyl]-amine (ex. 39);
(7-Benzyl-5,6-dimethyl-7H-pyrrolo[2,3-d]pyrimidin-4-yl)-[2-(3-fluoro-phenyl)-ethyl]-amine (ex. 43);
[2-(4-Amino-phenyl)-ethyl]-(7-benzyl-5,6-dimethyl-7H-pyrrolo[2,3-d]pyrimidin-4-yl)-amine (ex. 1);
(7-Benzyl-5,6-dimethyl-7H-pyrrolo[2,3-d]pyrimidin-4-yl)-[2-(4-dimethylamino-phenyl)-ethyl]-amine (ex. 62); and
[2-(4-Amino-phenyl)-ethyl]-[7-(3-dimethylamino-propyl)-5,6-dimethyl-7H-pyrrolo[2,3-d]pyrimidin-4-yl]-amine (ex. 12).

8. The invention further relates to pharmaceutical composition comprising one or more compound(s) of general formula (I) according to any of above points 1 to 7 or their solvates, hydrates, pharmaceutically acceptable salts or mixtures thereof as active ingredient together with one or more pharmaceutical auxiliary material(s).

9. The invention further relates to compounds according to any of above points 1 to 7 or the pharmaceutical composition according to any of above point 8 for use in the treatment and/or prevention of acute neurogenic inflammation and/or neuropathic hyperalgesia.

10. The invention further relates to compounds or the pharmaceutical composition for use according to above point 9, wherein the neurogenic inflammation comprises rheumatoid arthritis, allergic contact dermatitis, psoriasis, asthma and inflammatory bowel diseases.

A further aspect of the present invention is a method for preventing and/or treating inflammation, which method comprises administering to the mammal an amount of at least one compound of the present invention, effective to prevent and/or treat said inflammatory disease.

DETAILED DESCRIPTION OF THE INVENTION

In the context of this description the phrase "neurogenic inflammation related disease" embraces rheumatoid arthritis, allergic contact dermatitis, psoriasis, asthma and inflammatory bowel diseases. The "neuropathic pain" expression is used in the following cases: the pain is caused by damage or disease that affects the somatosensory system: postoperative pain, traumatic mononeuropathy, mechanical and thermal hyperalgesia. Neuropathic pain may be divided into peripheral neuropathic pain (in herpes zoster infection, HIV-related neuropathies, nutritional deficiencies, and toxins, remote manifestations of malignancies, immune mediated disorders and physical trauma to a nerve trunk), and central neuropathic pain (in spinal cord injury, multiple sclerosis and some strokes).

As used herein, the term "halogen" means fluorine, chlorine, bromine or iodine.

As used herein, the term "alkyl" alone or in combinations means a straight or branched-chain hydrocarbon group containing from 1 to 4, preferably 1 to 3 carbon atom(s) or 1 to 2 carbon atom(s) (i.e. "C$_{1-4}$" or "C$_{1-3}$" or "C$_{1-2}$" alkyl groups), such as methyl, ethyl, propyl, isopropyl, butyl, sec-butyl and t-butyl. In preferred cases this phrase can relate to alkyl groups containing 1 to 3 or 1 to 2 carbon atom(s) (i.e. "C$_{1-3}$" or "C$_{1-2}$" alkyl groups). In another preferred embodiment alkyl is methyl.

As used herein, the term "alkoxy" means an alkyl-O— group in which the alkyl group is as previously described. Non-limiting examples of suitable alkoxy groups include methoxy, ethoxy, n-propoxy, isopropoxy and n-butoxy, preferably methoxy. The bond to the parent moiety is through the ether oxygen. If the alkoxy group is substituted with halogen then it is named as haloalkoxy group.

As used herein, the term "aryl" refers to a mono- or bicyclic aromatic ring, e.g. phenyl or naphtyl, preferably phenyl.

As used herein, the term heteroaryl refers to a mono- or bicyclic aromatic ring system with 4 to 9 carbon atoms and 1 to 4 heteroatom(s) selected from the group of N, O and S, preferably furan-2-yl, pyridine-2-yl, pyridine-3-yl, pyridine-4-yl, thien-2-yl, pyrimidin-2-yl, pyrimidin-4-yl or piperazin-2-yl. In a highly preferred embodiment heteroaryl is furan-2-yl or bromo-pyridine-3-yl.

Those substituted aryl and heteroaryl groups are also within the scope, which contain substituent usually applied in the organic chemistry for substitution of aromatic and heteroaromatic groups (e.g. halogen, alkyl, alkoxy, hydroxyl, amino, optionally mono- or disubstituted with alkyl or —SO$_2$-alkyl, amide, urea, acylamino, alkylthio, alkylsulfinyl, alkylsulfonyl and cyano). Said substituents of aryl and heteroaryl groups may be further substituted with alkyl, amino optionally substituted with alkyl, or aryl. However, in the meaning of R1 the substituent cannot be alkoxy. Further, in the meaning of R1, monosubstitution with halogen is especially preferred.

In the meaning of R1, the term "RaRbN—(C1-4 alkyl), where Ra and Rb are independently from each other C1-4 alkyl" refers preferably to a [CH$_3$—(CH$_2$)$_n$]$_2$N—CH$_2$—(CH$_2$)$_n$ group, where n is 0, 1 or 2.

In the meaning of R2 and R3, the term "C1-4 alkyl" preferably refers to the following possibilities: methyl, ethyl, propyl, isopropyl, more preferably methyl. It is also preferred when one of R2 and R3 means hydrogen or both of them are hydrogen.

R4 represents preferably phenyl or substituted phenyl group where at least one of the substituents is at para position, which is selected from these possibilities: halogen, hydroxyl alkoxy, —NH$_2$, —N(CH$_3$)$_2$, isoindole-1,3-dione-2-yl, —NHCOR7, —NHSO$_2$R7, —NHCONHR7.

R5 is hydrogen or hydroxyl, preferably hydrogen.

R6 is hydrogen or alkyl, preferably hydrogen or methyl, more preferably hydrogen.

The preferred meaning of R7 can be selected from the following possibilities: C1-3 alkyl, phenyl, substituted phenyl, C1-2 alkyl-CO—C1-2 alkoxy, di(C1-3alkyl)amino. More preferably, R7 is methyl group or substituted phenyl group containing one or two substituents from the following group: C1-3 alkyl, halogen, C1-3 alkoxy and trifluoromethyl. Most preferably, R7 is dimethylamino or diethylamino.

The term "salt" means any ionic compound formed between one of the embodiments of the present invention and an acidic or basic molecule that can donate or accept ionic particle to/from its partner. The quaternary amine salts are also included.

Pharmaceutically acceptable (i.e., non-toxic, physiologically acceptable) salts are preferred, although other salts are also useful, e.g. for preparatory work. Salts of the compounds of the formula (I) may be formed, for example, by reacting a compound of formula (I) with an amount of acid or base, such as an equivalent amount, in a medium in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are known.

The term "solvate" means a compound formed by the combination of solvent molecules with molecules or ions of the solute (solvation). Solute can be any of the embodiments of the present invention and the solvent can be water (forming hydrates) or any organic solvent.

Another subject of the invention is providing pharmaceutical composition containing as active ingredient one or more compound(s) of general formula (I) together with one or more usual pharmaceutical auxiliary material(s). Formally another subject is the use of the compounds of general formula (I) in preparing such compositions. The applicable auxiliary materials are those which are generally applied in the preparation of pharmaceutical compositions, e.g. carriers, excipients, diluents, vehicles, coloring agents, flavoring agents, stabilizers, surfactants; carriers etc. for the preparation of sustained release compositions etc. Further details can be found in the following book: Comprehensive Medicinal Chemistry (Corwin Hansch; Chairman of Editorial Board), Pergamon Press 1990, Volume 5., Chapter 25.2).

Materials and Methods
General Methods
Synthetic Methods:

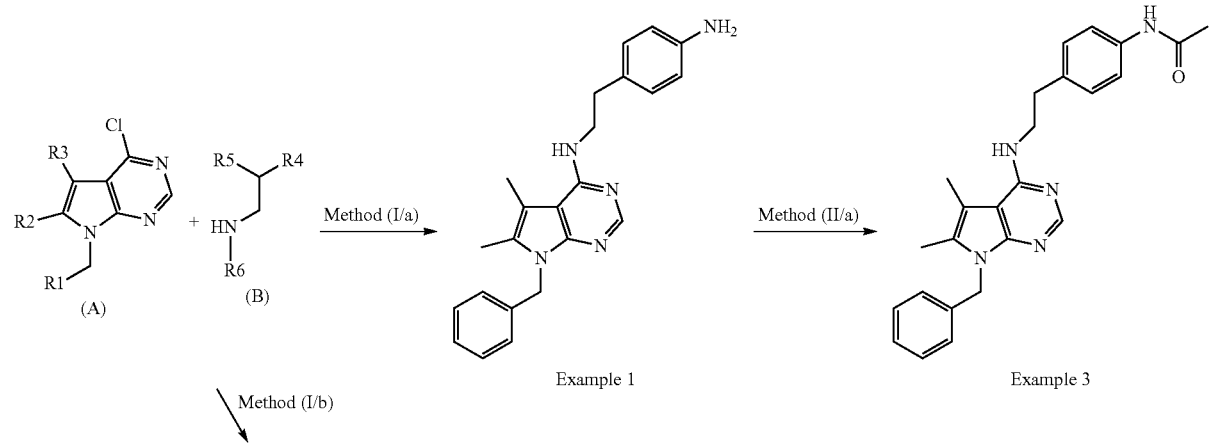

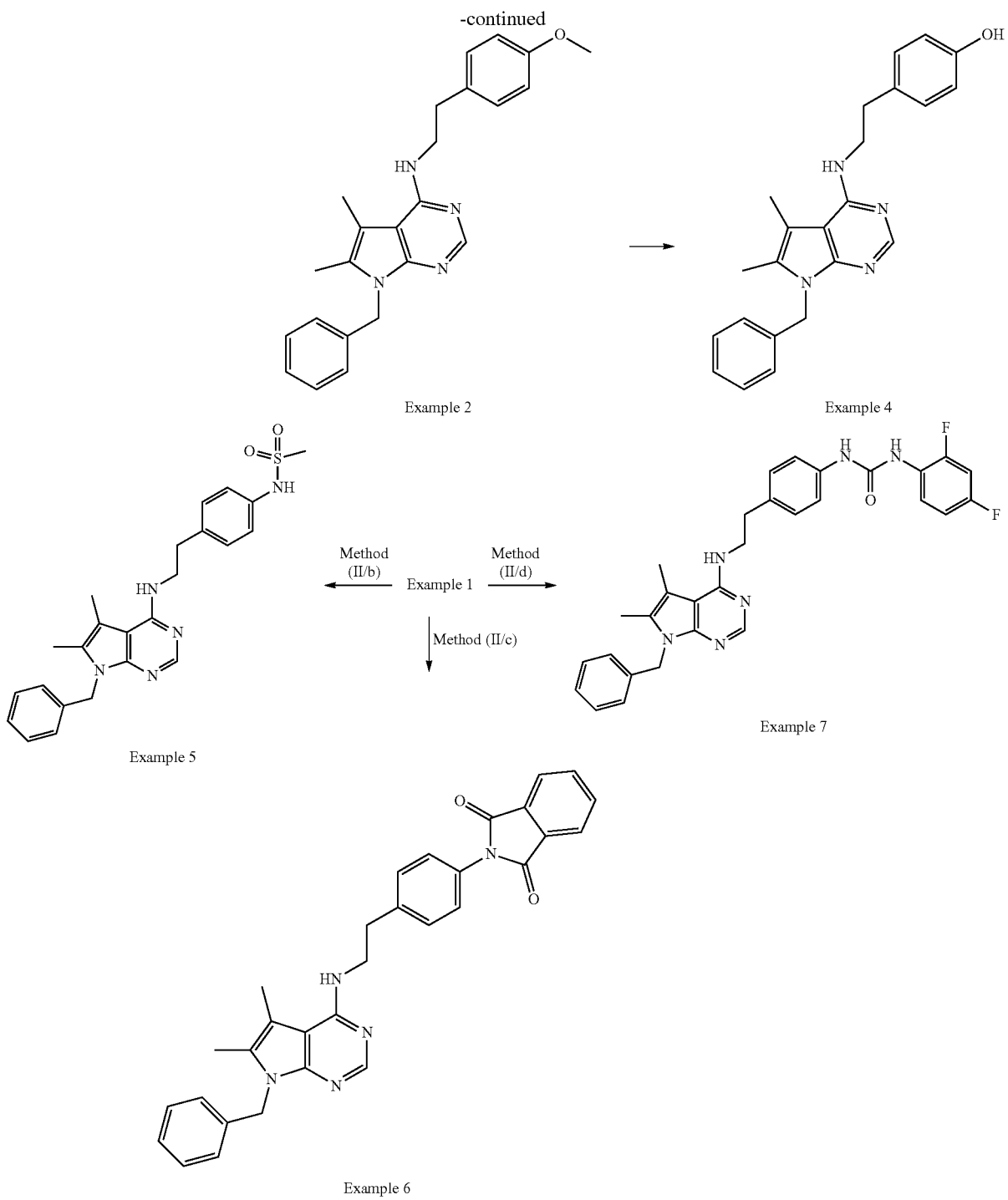

The subject molecules of the present invention were synthesized from starting compounds of general formula (A) by general method (I) and using commercially available variable amine starting materials (B). In order to enhance biological activity further derivatisation with acyl chlorides, sulfonyl chlorides or carbonic acid anhydrides—using general method (II)—were made in those cases, when a bifunctional amin [4-(2-Amino-ethyl)-phenylamine] had been used as starting amine (B). In biological point of view, demethylation of methoxy group on phenethylamino moiety by general method (III) is also preferred.

Synthesis of general formula (A) type compounds, i.e. 4-chloro-7H-pyrrolo[2,3-d]pyrimidines are well known in the literature and most of them are commercially available as well:

1. Pichler, Herbert; Folkers, Gerd; Roth, Hermann J.; Eger, Kurt, Liebigs Annalen der Chemie, 1986, #9 p. 1485-1505

2. Traxler, Peter M.; Furet, Pascal; Mett, Helmut; Buchdunger, Elisabeth; Meyer, Thomas; Lydon, Nicholas, Journal of Medicinal Chemistry, 1996, vol. 39, #12 p. 2285-2292

3. SZOLCSANYI, Janos; ORFI, Laszlo; KERI, Gyoergy; WACZEK, Frigyes; PINTER, Erika; HELYES, Zsuzsanna; SZUeTS, Tamas; NEMETH, Jozsef, Patent: WO2005/105804 A1, 2005; Location in patent: Page/Page column 17; 19; 22

General Method (I/a)

Iminoyl chloride (A) is heated in the mixture (2:1) of dimethylsulfoxide and amine reagent (B). The reaction mixture is treated with water and the product is extracted with ethyl acetate followed by purification with column chromatography. Compounds of Examples 1, 8, 9, 10, 11 and 12 were synthesized using this method.

General Method (I/b)

1 equivalent of iminoyl chloride (A) is heated in the presence of 2 equivalent of amine reagent (B). Ethyl acetate is added after completion of the reaction and the hydrochloride salt of the excess of amine reagent is removed by filtration. Compounds of Examples 2 and 13-43 were synthesized using this method.

General Method (I/c)

Mixture of 1 equivalent of iminoyl chloride (A) and 2 equivalent of amine reagent (B) is heated in DMSO. After completion of the reaction 1 N aqueous solution of hydrochloric acid is added and this crude product is collected by filtration and washed with water. The pure product is obtained by chromatography, applying the solution of the crude product directly onto preparative TLC.

EXAMPLE 1

[2-(4-Amino-phenyl)-ethyl]-(7-benzyl-5,6-dimethyl-7H-pyrrolo[2,3-d]pyrimidin-4-yl)-amine 1.5 g (5.5 mmol) of 7-benzyl-4-chloro-5,6-dimethyl-7H-pyrrolo[2,3-d]pyrimidine was heated in the mixture of 2.75 ml 4-(2-amino-ethyl)-phenylamine and 5.5 ml dimethylsulfoxide at 100° C. for 4 hours, then 200 ml water was added and the product was extracted with 2*100 ml ethyl acetate. The fused organic extracts were dried over anhydrous sodium sulfate and the solvent was removed under reduced pressure. The crude product was purified by column chromatography (silica gel 60/chloroform:methanol=95:5) The crystalline product was obtained from diethyl ether (yield: 1.4 g (68%)).

EXAMPLE 2

(7-Benzyl-5,6-dimethyl-7H-pyrrolo[2,3-d]pyrimidin-4-yl)-[2-(4-methoxy-phenyl)-ethyl]-amine 1.36 g (5 mmol) of 7-benzyl-4-chloro-5,6-dimethyl-7H-pyrrolo[2,3-d]pyrimidine was treated with 1.51 g (10 mmol) of 2-(4-methoxy-phenyl)-ethylamine at 100° C. for 2 hours followed by overnight stirring at room temperature, then 100 ml of 1N aqueous hydrochloric acid solution was added and the precipitated product was collected by filtration. This crude product was partitioned between 200 ml of ethyl acetate and 100 ml aqueous solution of saturated sodium bicarbonate. The organic phase was separated, dried over sodium sulfate and concentrated under reduced pressure. The analytically pure product was obtained from diethyl ether (yield: 1.196 g (61%)).

EXAMPLE 23

[7-(3-Chloro-benzyl)-5,6-dimethyl-7H-pyrrolo[2,3-d]pyrimidin-4-yl]-[2-(4-methoxy-phenyl)-ethyl]-amine 0.153 g (0.5 mmol) of 74-Chloro-7-(3-chloro-benzyl)-5,6-dimethyl-7H-pyrrolo[2,3-d]pyrimidine was treated with 0.25 ml of 2-(4-methoxy-phenyl)-ethylamine in 0.5 ml DMSO at 100° C. for 2 hours followed by overnight stirring at room temperature, then 100 ml of 1N aqueous hydrochloric acid solution was added and the precipitated product was collected by filtration. This crude product was dissolved in the mixture of chloroform:methanol=1:1 and this solution was applied for purification on two preparative TLC plates. (Merck PLC silica gel 60 F254, 1 mm/chloroform:Methanol=95:5) The product was crystallized from diizopropyl ether. i (yield: 0.12 g (57%)).

General Method (II/a)

1 equivalent of (4-aminophenyl)ethylamine derivate is treated with 1.1 equivalent of acyl chloride in pyridine at room temperature. The solvent is removed after completion of the reaction, then ethyl acetate and 5% solution of sodium bicarbonate are added. The pure product is obtained from the organic phase. The compounds of Examples 3 and 44-53 were synthesized using this method.

EXAMPLE 3

4-N-{4-[2-(7-Benzyl-5,6-dimethyl-7H-pyrrolo[2,3-d]pyrimidin-4-ylamino)-ethyl]-phenyl}-acetamide 0.8 g (2.15 mmol) of [2-(4-amino-phenyl)-ethyl]-(7-benzyl-5,6-dimethyl-7H-pyrrolo[2,3-d]pyrimidin-4-yl)-amine was treated with 0.186 g (2.36 mmol) acetyl chloride in 4.5 ml pyridine at room temperature. The mixture was stirred overnight and the solvent was removed after completion of the reaction, then 100 ml of ethyl acetate and 50 ml of 5% solution of sodium bicarbonate were added. The ethyl acetate phase was separated, dried over anhydrous sodium sulfate and concentrated, then diisopropyl ether was added and product was filtered off (yield: 0.505 g (56%)).

General Method (II/b)

1 equivalent of adequate (4-aminophenyl)ethylamine derivate is treated with 1.1 equivalent of sulfonyl chloride in pyridine at room temperature. The solvent is removed after completion of the reaction, then ethyl acetate and 5% solution of sodium bicarbonate are added. The pure product is obtained from the organic phase. The compounds of Examples 5 and 54 and 55 were synthesized using this method.

EXAMPLE 5

N-{4-[2-(7-Benzyl-5,6-dimethyl-7H-pyrrolo[2,3-d]pyrimidin-4-ylamino)-ethyl]-phenyl}-methanesulfonamide 0.186 g (0.5 mmol) of [2-(4-amino-phenyl)-ethyl]-(7-benzyl-5,6-dimethyl-7H-pyrrolo[2,3-d]pyrimidin-4-yl)-amine was treated with 0.04 ml (0.55 mmol) acetyl chloride in 1.5 ml pyridine at room temperature. The mixture was stirred overnight and the solvent was removed after completion of the reaction, then 20 ml of ethyl acetate and 10 ml of 5% solution of sodium bicarbonate were added. The ethyl acetate phase was separated, dried over anhydrous sodium sulfate and concentrated, then diisopropyl ether was added and product was filtered off (yield: 0.14 g (62%)).

General Method (II/c)

1 equivalent of adequate (4-aminophenyl)ethylamine derivate is treated with 1 equivalent of acid anhydride in dimethyl formamide at 120° C. After completion of the reaction ethyl acetate and water are added. The product is obtained from the organic phase. The compounds of examples 6 and 56 were synthesized using this method.

EXAMPLE 6

2-{4-[2-(7-Benzyl-5,6-dimethyl-7H-pyrrolo[2,3-d]pyrimidin-4-ylamino)-ethyl]-phenyl}-isoindole-1,3-dione 0.185 g (0.5 mmol) of [2-(4-amino-phenyl)-ethyl]-(7-benzyl-5,6-dimethyl-7H-pyrrolo[2,3-d]pyrimidin-4-yl)-amine was treated with 0.075 g (0.5 mmol) phthalic anhydride in 0.5 dimethyl formamide at room temperature for 1 hour followed by heating at 120° C. for 2 hours. After that ethyl acetate and water were added and the crude product was filtered off and purified on prep TLC (chloroform:methanol=95:5). The pure product was obtained crystallized from diethylether (yield: 0.095 g (38%)).

General Method (II/d)

1 equivalent of adequate (4-aminophenyl)ethylamine derivate is treated with 1.1 equivalent of the corresponding isocyanate reagent in dimethyl formamide at room temperature. The product is isolated from ethyl acetate, which is added after the dimethyl formamide has been removed. Examples 7 and 57 were synthesized using this method.

EXAMPLE 7

1-{4-[2-(7-Benzyl-5,6-dimethyl-7H-pyrrolo[2,3-d]pyrimidin-4-ylamino)-ethyl]-phenyl}-3-(2,4-difluoro-phenyl)-urea 0.185 g (0.5 mmol) of [2-(4-amino-phenyl)-ethyl]-(7-benzyl-5,6-dimethyl-7H-pyrrolo[2,3-d]pyrimidin-4-yl)-amine was treated with 0.064 ml (0.5 mmol) 2,4-difluorophenyl isocyanate in 1.5 ml dimethyl formamide at room temperature. The solvent was removed after 1 week stirring and ethyl acetate was added, and then the precipitated product was isolated by filtration (yield: 0.05 g (20%)).

General Method (III)

1 equivalent of adequate methyoxyphenylethylamine derivate is treated with at least 2.5 equivalent of boron tribromide in dichloromethane at room temperature. Ice, ethyl acetate and 5% solution of sodium bicarbonate are added after completion of the reaction. The pure product is obtained from the organic phase. Examples 4 and 58-61 were synthesized using this method.

EXAMPLE 4

(4-[2-(7-Benzyl-5,6-dimethyl-7H-pyrrolo[2,3-d]pyrimidin-4-ylamino)-ethyl]-phenol 0.56 g (1.4 mmol) of (7-benzyl-5,6-dimethyl-7H-pyrrolo[2,3-d]pyrimidin-4-yl)-[2-(4-methoxy-phenye-ethyl]-amine was dissolved in 3 ml of dichloromethane and was treated with 3.6 ml of 1M boron tribromide solution in dichloromethane at room temperature. The reaction mixture was stirred overnight, then 50 ml of ice, 100 ml of ethyl acetate and 10 ml of saturated solution of sodium bicarbonate were added. After 15 min stirring the organic layer was separated, dried over anhydrous sodium sulfate and concentrated under reduced pressure. The pure product was obtained from diisopropyl ether (yield: 0.316 g (58%)).

Method IV

The primary amino derivate is dissolved in the mixture of methanol and glacial acetic acid and treated with paraformaldehyde in the presence of cyanoborohydride. Water is added after completion of the reaction and the product is extracted with ethyl acetate and purified by prep TLC.

EXAMPLE 62

(7-Benzyl-5,6-dimethyl-7H-pyrrolo[2,3-d]pyrimidin-4-yl)-[2-(4-dimethylamino-phenyl)-ethyl]-amine 0.371 g (1 mmol) of [2-(4-amino-phenyl)-ethyl]-(7-benzyl-5,6-dimethyl-7H-pyrrolo[2,3-d]pyrimidin-4-yl)-amine was dissolved in the mixture of 4 ml methanol, 0.1 ml glacial acetic acid and 0.1 g of paraformaldehyde, after 30 min stirring at room temperature 0.12 g of sodium cyanoborohydride was added. The reaction was monitored by TLC and water was added after the starting material disappeared. The product was extracted with ethyl acetate and purified by prep TLC (chloroform:methanol=95:5). The pure product was obtained from diethylether (yield: 0.07 g (17%)).

Method V: Preparation of Hydrochloric Salt of the Prepared Compounds

The base is dissolved in pure ethyl acetate or in the mixture of ethyl acetate and ethanol followed by addition of 4 M solution of hydrochloric acid in dioxan. The hydrochloric acid is used in excess (2-5 equivalents). The crystalline product is collected by filtration and washed with ethyl acetate.

Analytical Characterization

All of the prepared compounds were characterized by three independent analytical methods.

NMR

The 300 MHz $^1$H-NMR analysis was performed with an apparatus of type Bruker AVANCE-300 at 25° C., exact frequency was 300.14 MHz. Generally DMSO-$d_6$ was used as solvent, exceptions given. Chemical shifts are given in parts per million (S) referenced to TMS ($\delta$=0.00 ppm).

LCMS

The LCMS analysis was performed with a liquid chromatography mass-spectrometer Waters chromatograph with the following parameters:

Waters HPLC/MS:
MS detector: Waters SQD
UV detector: Waters 996 DAD
Separation module: Waters Alliance 2795
HPLC:
Column: Waters XBridge C18, 50 mm×4.6 mm, 3.5 µm
Solvent I: Water/0.1% HCOOH
Solvent II: AcCN
Acetonitrile: Riedel-deHaën; G Chromasolv (34998)
Water: Mili-Q Academic
Formic acid: Riedel-deHaën; extra pure (27001)
Flow rate: 2 ml/min
Injection: 5 µg
Gradient:

| Method | | |
|---|---|---|
| time | Solv. I. | Solv. II. |
| 0.00 min | 95% | 5% |
| 0.50 min | 95% | 5% |
| 5.50 min | 5% | 95% |
| 6.00 min | 5% | 95% |
| 6.50 min | 95% | 5% |
| 7.00 min | 95% | 5% |

MS: Ionization: ES⁺/ES⁻
Source block temperature: 110° C.
Desolvation temperature: 250° C.
Desolvation gas: 500 L/h
Cone gas: 80 L/h
Capillary voltage: 3000 V Cone voltage: 30 V
Extractor voltage: 6 V
Rf lens voltage: 0.1 V
Scan: 80 to 1000 m/z in 1 sec.
Inter-scan delay: 0.1 s

| Expl No | Structure | AutoNom Name | NMR Assign | Melting point (C. °) | Method |
|---|---|---|---|---|---|
| 1 | 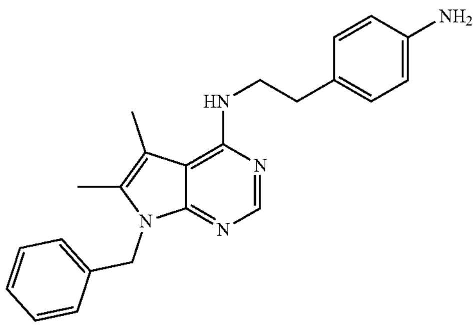 [SMILES: Cc1c(C)n(Cc2ccccc2)c2ncnc(NCCc3ccc(N)cc3)c12] | [2-(4-Amino-phenyl)-ethyl]-(7-benzyl-5,6-dimethyl-7H-pyrrolo[2,3-d]pyrimidin-4-yl)-amine | 8.09 (s, 1H), 7.26 (m, 3H), 7.03 (d, 2H), 6.92 (d, 2H), 6.52 (d, 2H), 6.28 (t, 1H), 5.33 (s, 2H), 4.86 (s, 2H), 3.60 (q, 2H), 2.73 (t, 2H), 2.26 (s, H), 2.13 (s, 3H) | 150.7-151.8 | Ia |
| 2 | 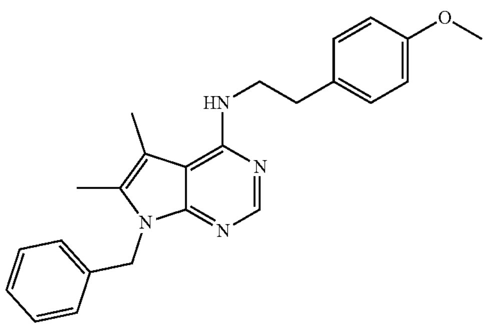 [SMILES: COc1ccc(CCNc2ncnc3c2c(C)c(C)n3Cc2ccccc2)cc1] | (7-Benzyl-5,6-dimethyl-7H-pyrrolo[2,3-d]pyrimidin-4-yl)-[2-(4-methoxy-phenyl)-ethyl]-amine | 8.27 (s, 1H), 8.00 (bs, 1H), 7.26 (m, 4H), 7.07 (d, 2H), 6.96 (t, 1H), 6.90 (d, 1H), 6.79 (m, 1H), 5.45 (s, 2H), 3.86 (q, 2H), 3.73 (s, 3H), 2.98 (t, 2H), 2.33 (s, 3H), 2.20 (s, 3H) | 100-101.9 | Ib |
| 3 | 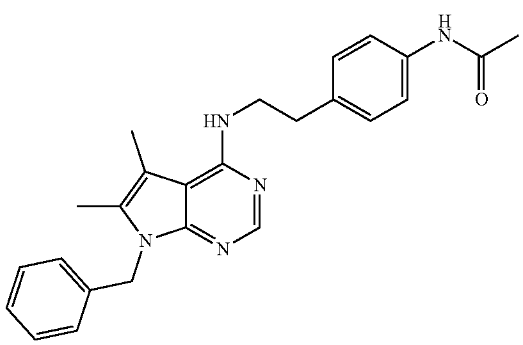 [SMILES: CC(=O)Nc1ccc(CCNc2ncnc3c2c(C)c(C)n3Cc2ccccc2)cc1] | N-{4-[2-(7-Benzyl-5,6-dimethyl-7H-pyrrolo[2,3-d]pyrimidin-4-ylamino)-ethyl]-phenyl}-acetamide | 9.83 (s, 1H), 8.10 (s, 1H), 7.51 (d, 2H), 7.30-7.21 (m, 3H), 7.18 (d, 2H), 7.03 (d, 2H), 6.35 (t, 1H), 5.34 (s, 2H), 3.68 (q, 2H), 2.87 (t, 2H), 2.27 (s, 3H), 2.13 (s, 3H), 2.02 (s, 3H) | 186.9-187.7 | IIa |
| 4 | 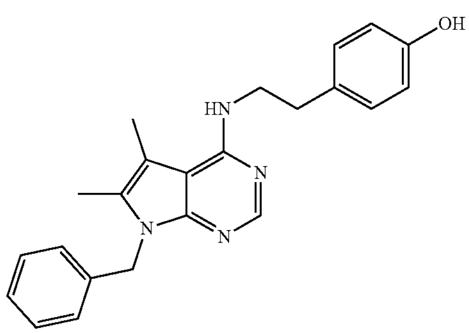 [SMILES: Cc1c(C)n(Cc2ccccc2)c2ncnc(NCCc3ccc(O)cc3)c12] | 4-[2-(7-Benzyl-5,6-dimethyl-7H-pyrrolo[2,3-d]pyrimidin-4-ylamino)-ethyl]-phenol | 9.15 (bs, 1H), 8.10 (s, 1H), 7.26 (m, 3H), 7.04 (m, 4H), 6.70 (d, 2H), 6.31 (t, 1H), 5.34 (s, 2H), 3.64 (q, 2H), 2.80 (t, 2H), 2.26 (s, 3H), 2.13 (s, 3H) | 198-199 | III |

-continued

| Expl No | Structure | AutoNom Name | NMR Assign | Melting point (C. °) | Method |
|---|---|---|---|---|---|
| 5 | 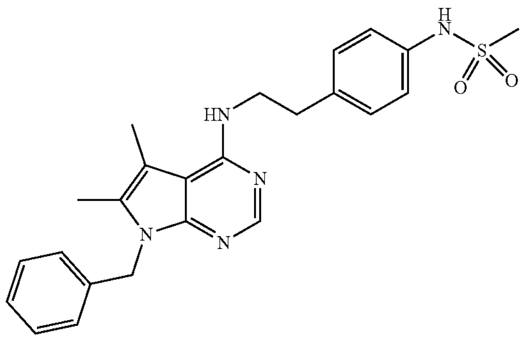 [SMILES: Cc1c(C)n(Cc2ccccc2)c2ncnc(NCCc3ccc(NS(C)(=O)=O)cc3)c12] | N-{4-[2-(7-Benzyl-5,6-dimethyl-7H-pyrrolo[2,3-d]pyrimidin-4-ylamino)-ethyl]-phenyl}-methanesulfonamide | 9.59 (bs, 1H), 8.10 (s, 1H), 7.31-7.24 (m, 5H), 7.21 (d, 2H), 7.03 (d, 2H), 6.40 (t, 1H), 5.34 (s, 2H), 3.68 (q, 2H), 2.93 (s, 3H), 2.88 (t, 2H), 2.67 (s, 3H), 2.13 (s, 3H) | 175.7-176.4 | IIb |
| 6 | 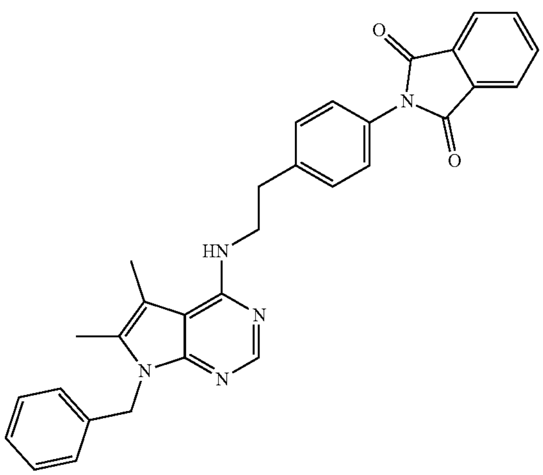 [SMILES: Cc1c(C)n(Cc2ccccc2)c2ncnc(NCCc3ccc(N4C(=O)c5ccccc5C4=O)cc3)c12] | 2-{4-[2-(7-Benzyl-5,6-dimethyl-7H-pyrrolo[2,3-d]pyrimidin-4-ylamino)-ethyl]-phenyl}-isoindole-1,3-dione | 8.13 (s, 1H), 7.94 (d, 4H), 7.40 (bs, 4H), 7.27 (m, 3H), 7.04 (m, 2H), 6.50 (m, 1H), 5.35 (s, 2H), 3.75 (bs, 2H), 3.01 (bs, 2H), 2.30 (s, 3H), 2.14 (s, 3H) | 219-221 | IIc |
| 7 | 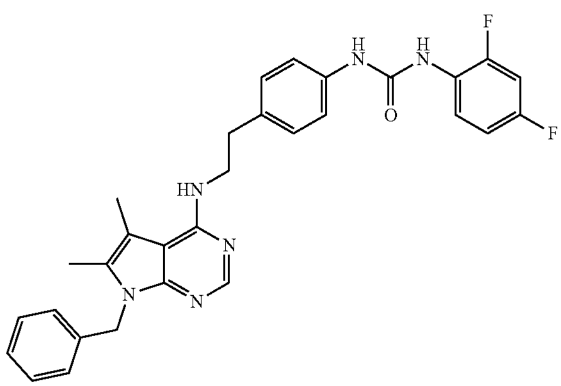 [SMILES: Cc1c(C)n(Cc2ccccc2)c2ncnc(NCCc3ccc(NC(=O)Nc4ccc(F)cc4F)cc3)c12] | 1-{4-[2-(7-Benzyl-5,6-dimethyl-7H-pyrrolo[2,3-d]pyrimidin-4-ylamino)-ethyl]-phenyl}-3-(2,4-difluoro-phenyl)-urea | 9.2 (bs, 1H), 8.5 (bs, 1H), 8.11 (s, 1H), 8.09 (m, 1H), 7.39 (d, 2H), 7.31-7.17 (m, 6H), 7.04 (bd, 3H), 6.36 (t, 1H), 5.34 (s, 2H), 3.67 (q, 2H), 2.87 (t, 2H), 2.28 (s, 3H), 2.13 (s, 3H) | 208-209.2 | IId |
| 8 | 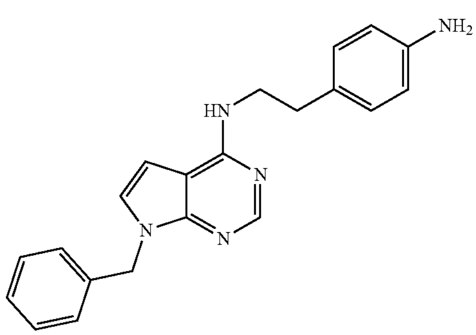 [SMILES: Nc1ccc(CCNc2ncnc3c2ccn3Cc2ccccc2)cc1] | [2-(4-Amino-phenyl)-ethyl]-(7-benzyl-7H-pyrrolo[2,3-d]pyrimidin-4-yl)-amine | 9.89 (bs, 1H), 8.34 (s, 1H), 7.56 (bs, 1H), 7.46 (d, 2H), 7.36-7.24 (m, 7H), 7.06 (d, 1H), 3.84 (q, 2H), 3.6 (bs, 2H), 3.02 (s, 2H), | >260 | Ia |

| Expl No | Structure | AutoNom Name | NMR Assign | Melting point (C. °) | Method |
|---|---|---|---|---|---|
| 9 | 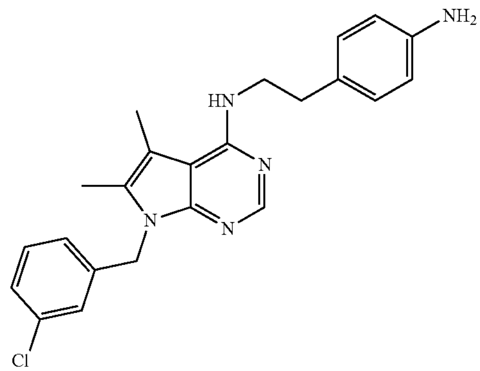 [SMILES: Cc1c(C)n(Cc2cccc(Cl)c2)c2ncnc(NCCc3ccc(N)cc3)c12] | [2-(4-Amino-phenyl)-ethyl]-[7-(3-chloro-benzyl)-5,6-dimethyl-7H-pyrrolo[2,3-d]pyrimidin-4-yl]-amine | 8.10 (s, 1H), 7.31 (d, 1H), 7.30 (s, 1H), 7.10 (s, 1H), 6.95 (d, 1H), 6.92 (d, 2H), 6.52 (d, 2H), 6.29 (t, 1H), 5.34 (s, 2H), 4.84 (bs, 2H), 3.61 (q, 2H), 2.74 (t, 2H), 2.27 (s, 3H), 2.14 (s, 3H) | | Ia |
| 10 | 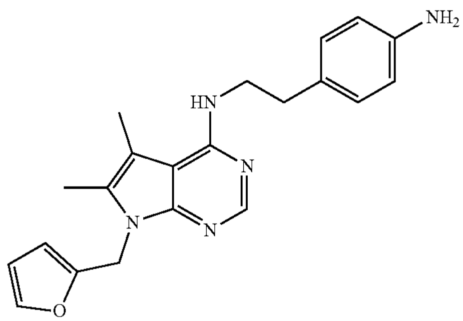 [SMILES: Cc1c(C)n(Cc2ccco2)c2ncnc(NCCc3ccc(N)cc3)c12] | [2-(4-Amino-phenyl)-ethyl]-(7-furan-2-ylmethyl-5,6-dimethyl-7H-pyrrolo[2,3-d]pyrimidin-4-yl)-amine | 8.09 (s, 1H), 7.53 (t, 1H), 6.91 (d, 2H), 6.51 (d, 2H), 6.36 (dd, 1H), 6.23 (m, 2H), 5.30 (s, 2H), 4.84 (bs, 2H), 3.82 (q, 2H), 2.71 (t, 2H), 2.26 (s, 3H), 2.24 (s, 3H) | 150-151.5 | Ia |
| 11 | 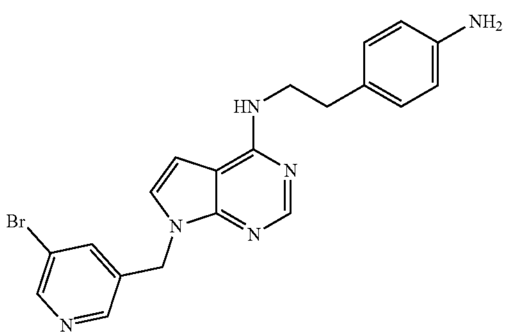 [SMILES: Nc1ccc(CCNc2ncnc3c2ccn3Cc2cncc(Br)c2)cc1] | [2-(4-Amino-phenyl)-ethyl]-[7-(5-bromo-pyridin-3-ylmethyl)-7H-pyrrolo[2,3-d]pyrimidin-4-yl]-amine | 8.60 (d, 1H), 8.48 (d, 1H), 8.17 (s, 1H), 7.88 (s, 1H), 7.57 (t, 1H), 7.27 (d, 1H), 6.90 (d, 2H), 6.61 (d, 1H), 6.50 (d, 2H), 5.38 (s, 2H), 4.82 (s, 2H), 3.58 (q, 2H), 2.72 (t, 2H) | 158.8-160.9 | Ia |
| 12 | 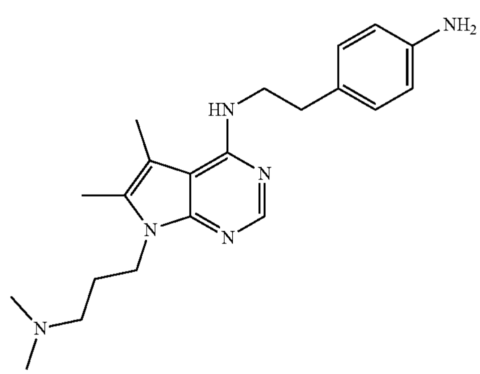 [SMILES: Cc1c(C)n(CCCN(C)C)c2ncnc(NCCc3ccc(N)cc3)c12] | [2-(4-Amino-phenyl)-ethyl]-[7-(3-dimethylamino-propyl)-5,6-dimethyl-7H-pyrrolo[2,3-d]pyrimidin-4-yl]-amine | 8.06 (s, 1H), 6.90 (d, 2H), 6.51 (d, 2H), 6.15 (t, 1H), 4.80 (bs, 2H), 4.06 (t, 2H), 3.58 (q, 2H), 2.71 (t, 2H), 2.25 (s, 6H), 2.18 (t, 2H), 2.16 (s, 6H), | 237.2-239.9 | Ia, V |

-continued

| Expl No | Structure | AutoNom Name | NMR Assign | Melting point (C. °) | Method |
|---|---|---|---|---|---|
| 13 | 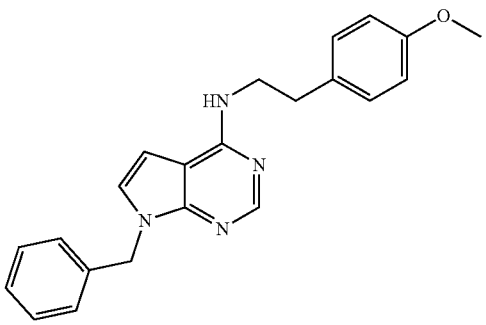 [SMILES: COc1ccc(CCNc2ncnc3c2ccn3Cc2ccccc2)cc1] | (7-Benzyl-7H-pyrrolo[2,3-d]pyrimidin-4-yl)-[2-(4-methoxy-phenyl)-ethyl]-amine | 8.17 (s, 1H), 7.55 (t, 1H), 7.32-7.16 (m, 8H), 6.86 (d, 2H), 6.58 (d, 1H), 5.33 (s, 2H), 3.71 (s, 3H), 3.64 (q, 2H), 2.85 (t, 2H), | 140-141 | Ic |
| 14 | 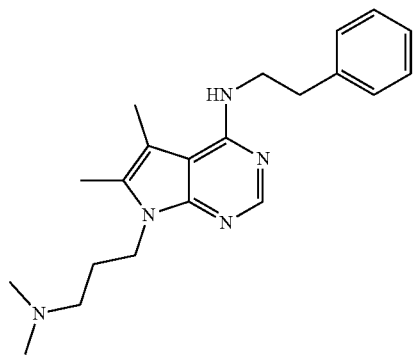 [SMILES: Cc1c(C)n(CCCN(C)C)c2ncnc(NCCc3ccccc3)c12] | [7-(3-Dimethylamino-propyl)-5,6-dimethyl-7H-pyrrolo[2,3-d]pyrimidin-4-yl]-phenethyl-amine | 10.84 (bs, 1H), 8.25 (s, 1H), 7.30 (m, 5H), 4.26 (t, 2H), 3.87 (q, 2H), 3.02 (m, 4H), 2.70 (s, 3H), 2.69 (s, 3H), 2.35 (s, 3H), 2.33 (s, 3H), 2.09 (m, 2H), | 236-238 | Ib, V |
| 15 | 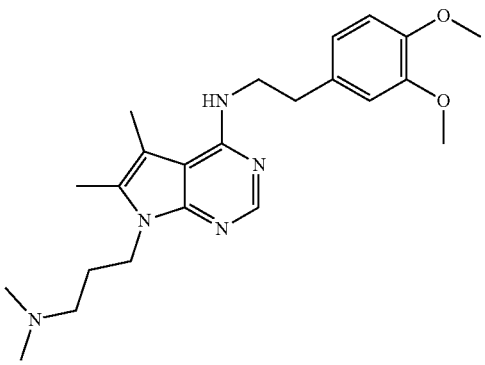 | [2-(3,4-Dimethoxy-phenyl)-ethyl]-[7-(3-dimethylamino-propyl)-5,6-dimethyl-7H-pyrrolo[2,3-d]pyrimidin-4-yl]-amine | 10.77 (bs, 1H), 8.24 (s, 1H), 8.02 (bs, 1H), 7.05 (s, 1H), 6.86 (m, 3H), 4.26 (m, 2H), 3.87 (q, 2H), 3.72 (s, 6H), 3.02 (bs, 2H ), 2.90 (t, 2H), 2.69 (s, 6H), 2.35 (s, 6H), 2.10 (m, 2H) | 156-158.2 | Ib, V |
| 16 | 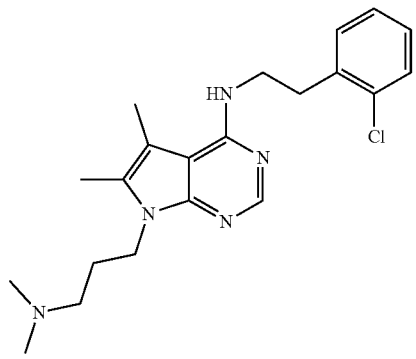 [SMILES: Cc1c(C)n(CCCN(C)C)c2ncnc(NCCc3ccccc3Cl)c12] | [2-(2-Chloro-phenyl)-ethyl]-[7-(3-dimethylamino-propyl)-5,6-dimethyl-7H-pyrrolo[2,3-d]pyrimidin-4-yl]-amine | 10.78 (bs, 1H), 8.27 (s, 1H), 7.94 (bs, 1H), 7.48 (d, 1H), 7.42 (d, 1H), 7.28 (m, 2H), 4.26 (t, 2H), 3.91 (q, 2H), 3.11 (t, 2H), 3.04 (bs, 2H), 2.70 (s, 6H), 2.36 (s, 3H), 2.39 (s, 3H), 2.09 (m, 2H) | 245-248 | Ic, V |

-continued

| Expl No | Structure | AutoNom Name | NMR Assign | Melting point (C. °) | Method |
|---|---|---|---|---|---|
| 17 | 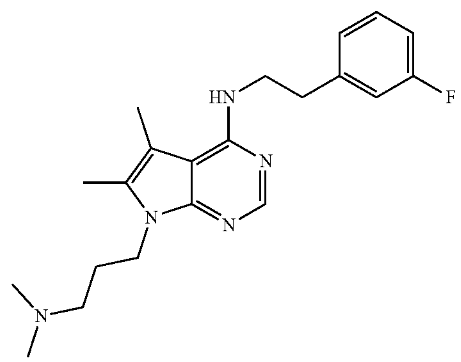 [SMILES: Cc1c(C)n(CCCN(C)C)c2ncnc(NCCc3cccc(F)c3)c12] | [7-(3-Dimethylamino-propyl)-5,6-dimethyl-7H-pyrrolo[2,3-d]pyrimidin-4-yl]-[2-(3-fluoro-phenyl)-ethyl]-amine | 14.2 (bs, 1H), 10.74 (bs, 1H), 8.26 (bs, 1H), 7.34 (dd, 2H), 7.26 (d, 1H), 7.18 (d, 1H), 7.05 (td, 1H), 4.26 (t, 2H), 3.88 (q, 2H), 3.00 (m, 4H), 2.70 (s, 6H), 2.35 (s, 3H), 2.33 (s, 3H), 2.08 (m, 2H) | 239-240.2 | Ib, V |
| 18 | 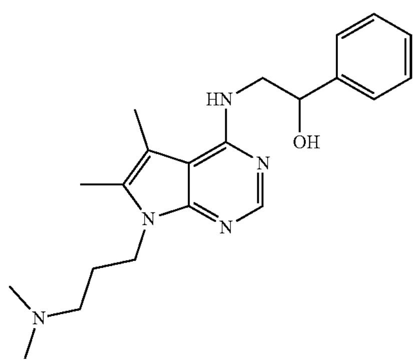 [SMILES: Cc1c(C)n(CCCN(C)C)c2ncnc(NCC(O)c3ccccc3)c12] | 2-[7-(3-Dimethylamino-propyl)-5,6-dimethyl-7H-pyrrolo[2,3-d]pyrimidin-4-ylamino]-1-phenyl-ethanol | 10.78 (bs, 1H), 8.27 (s, 1H), 7.85 (bs, 1H), 7.50 (d, 2H), 7.37 (t, 2H), 7.28 (t, 1H), 4.92 (t, 1H), 4.27 (t, 2H), 3.81 (m, 2H), 3.04 (bs, 2H), 2.70 (s, 6H), 2.37 (s, 6H), 2.10 (m, 2H), | 209-212.9 | Ib, V |
| 19 | 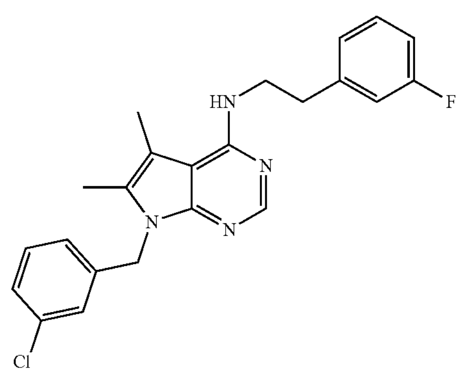 [SMILES: Cc1c(C)n(Cc2cccc(Cl)c2)c2ncnc(NCCc3cccc(F)c3)c12] | [7-(3-Chloro-benzyl)-5,6-dimethyl-7H-pyrrolo[2,3-d]pyrimidin-4-yl]-[2-(3-fluoro-phenyl)-ethyl]-amine | 8.28 (s, 1H), 8.03 (bs, 1H), 7.35 (m, 3H), 7.24 (d, 1H), 7.19-6.99 (m, 5H), 5.47 (s, 2H), 3.87 (q, 2H), 3.02 (t, 2H), 2.33 (s, 3H), 2.21 (s, 3H) | 232-235 | Ic |
| 20 | 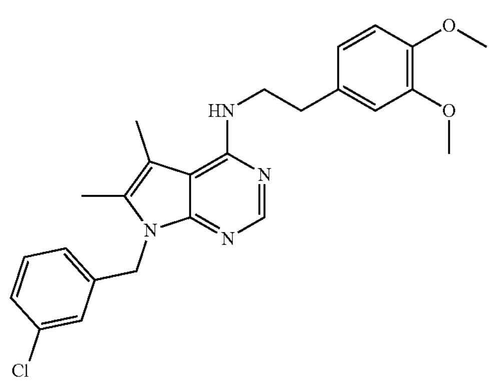 [SMILES: COc1ccc(CCNc2ncnc3c2c(C)c(C)n3Cc2cccc(Cl)c2)cc1OC] | [7-(3-Chloro-benzyl)-5,6-dimethyl-7H-pyrrolo[2,3-d]pyrimidin-4-yl]-[2-(3,4-dimethoxy-phenyl)-ethyl]-amine | 8.27 (s, 1H), 7.96 (bs, 1H), 7.35 (m, 2H), 7.17 (s, 1H), 6.98 (bs, 2H), 6.84 (m, 2H), 5.46 (s, 2H), 3.83 (q, 2H), 3.72 (s, 3H), 3.70 (s, 3H), 2.91 (t, 2H), 2.34 (s, 3H), 2.20 (s, 3H) | 118-120 | Ic |

-continued

| Expl No | Structure | AutoNom Name | NMR Assign | Melting point (C. °) | Method |
|---|---|---|---|---|---|
| 21 | 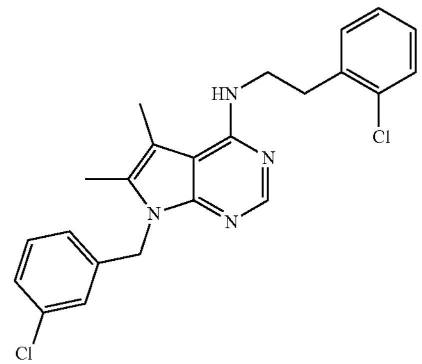 [SMILES: Cc1c(C)n(Cc2cccc(Cl)c2)c2ncnc(NCCc3ccccc3Cl)c12] | [7-(3-Chloro-benzyl)-5,6-dimethyl-7H-pyrrolo[2,3-d]pyrimidin-4-yl]-[2-(2-chloro-phenyl)-ethyl]-amine | 8.29 (s, 1H), 7.98 (bs, 1H), 7.49 (m, 1H), 7.43 (m, 1H), 7.34 (m, 2H), 7.28 (m, 2H), 7.14 (s, 1H), 7.01 (t, 1H), 5.47 (s, 2H), 3.90 (q, 2H), 3.13 (t, 2H), 2.29 (s, 3H), 2.20 (s, 3H) | 190-192 | Ic |
| 22 | 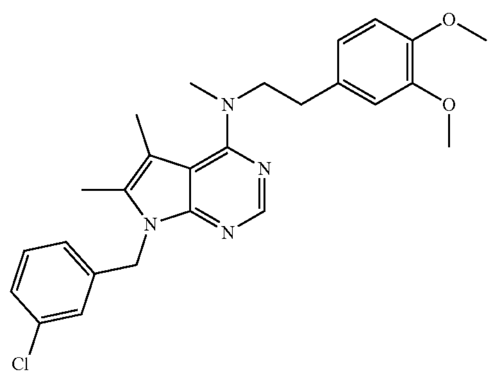 [SMILES: COc1ccc(CCN(C)c2ncnc3c2c(C)c(C)n3Cc2cccc(Cl)c2)cc1OC] | [7-(3-Chloro-benzyl)-5,6-dimethyl-7H-pyrrolo[2,3-d]pyrimidin-4-yl]-[2-(3,4-dimethoxy-phenyl)-ethyl]-methyl-amine | 8.26 (s, 1H), 7.35 (m, 2H), 7.19 (s, 1H), 6.96 (t, 1H), 6.82 (s, 1H), 6.73 (m, 2H), 5.49 (s, 2H), 4.00 (t, 2H), 3.66 (s, 3H), 3.60 (s, 3H), 3.27 (s, 3H), 2.93 (t, 2H), 2.25 (s, 3H), 3.24 (s, 3H) | 178-180 | Ic |
| 23 | 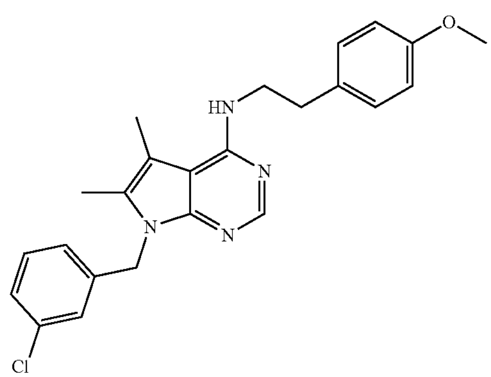 [SMILES: COc1ccc(CCNc2ncnc3c2c(C)c(C)n3Cc2cccc(Cl)c2)cc1] | [7-(3-Chloro-benzyl)-5,6-dimethyl-7H-pyrrolo[2,3-d]pyrimidin-4-yl]-[2-(4-methoxy-phenyl)-ethyl]-amine | 8.28 (s, 1H), 8.02 (bs, 1H), 7.35 (d, 1H), 7.34 (s, 1H), 7.27 (d, 2H), 7.17 (s, 1H), 6.99 (t, 1H), 6.87 (d, 2H), 5.47 (s, 2H), 3.80 (q, 2H), 3.17 (s, 3H), 2.91 (t, 2H), 2.34 (s, 3H), 2.21 (s, 3H) | 214-216 | Ic |
| 24 | 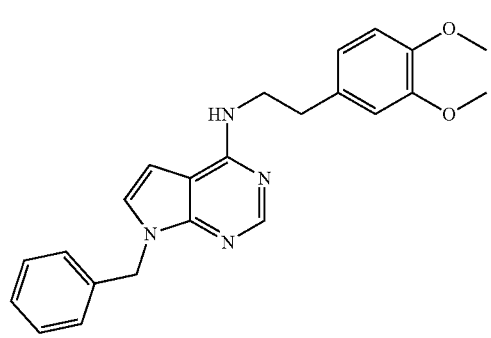 [SMILES: COc1ccc(CCNc2ncnc3c2ccn3Cc2ccccc2)cc1OC] | (7-Benzyl-7H-pyrrolo[2,3-d]pyrimidin-4-yl)-[2-(3,4-dimethoxy-phenyl)-ethyl]-amine | 9.71 (bs, 1H), 8.32 (s, 1H), 7.55 (d, 1H), 7.37-7.28 (m, 3H), 7.23 (d, 2H), 7.04 (d, 1H), 6.98 (s, 1H), 6.82 (m, 2H), 5.45 (s, 2H), 3.81 (q, 2H), 3.70 (s, 6H), 2.92 (t, 2H), | 177.3-178.3 | Ic |

-continued

| Expl No | Structure | AutoNom Name | NMR Assign | Melting point (C. °) | Method |
|---|---|---|---|---|---|
| 25 | 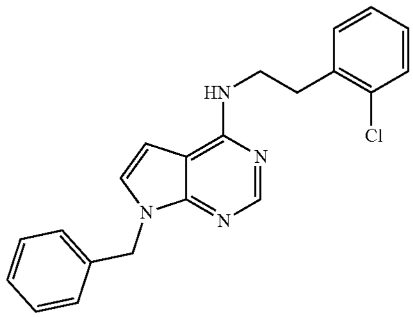 [SMILES: Clc1ccccc1CCNc1ncnc2c1ccn2Cc1ccccc1] | (7-Benzyl-7H-pyrrolo[2,3-d]pyrimidin-4-yl)-[2-(2-chloro-phenyl)-ethyl]-amine | 9.70 (bs, 1H), 8.36 (s, 1H), 7.53 (m, 2H), 7.44 (m, 1H), 7.36-7.23 (m, 7H), 7.01 (d, 1H), 5.46 (s, 2H), 3.83 (q, 2H), 5.46 (s, 2H), 3.13 (t, 2H) | 180-182.3 | Ic |
| 26 | 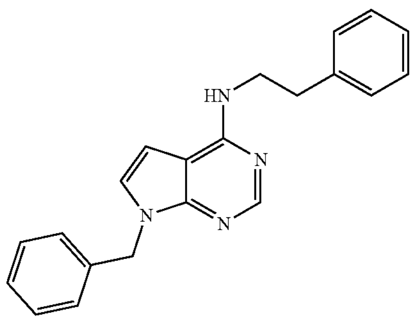 [SMILES: c1ccc(CCNc2ncnc3c2ccn3Cc2ccccc2)cc1] | (7-Benzyl-7H-pyrrolo[2,3-d]pyrimidin-4-yl)-phenethyl-amine | 9.78 (bs, 1H), 8.33 (s, 1H), 7.56 (d, 1H), 7.37-7.22 (m, 10H), 7.04 (d, 1H), 5.45 (s, 2H), 3.81 (q, 2H), 3.00 (t, 2H) | 210-211.8 | Ic |
| 27 | 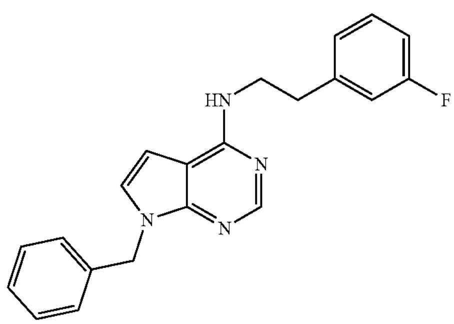 [SMILES: Fc1cccc(CCNc2ncnc3c2ccn3Cc2ccccc2)c1] | (7-Benzyl-7H-pyrrolo[2,3-d]pyrimidin-4-yl)-[2-(3-fluoro-phenyl)-ethyl]-amine | 8.17 (s, 1H), 7.59 (t, 1H), 7.36-7.19 (m, 7H), 7.10 (d, 2H), 7.01 (m, 1H), 6.58 (d, 1H), 5.33 (s, 2H), 3.70 (q, 2H), 2.94 (t, 2H) | 116-117.5 | Ic |
| 29 | 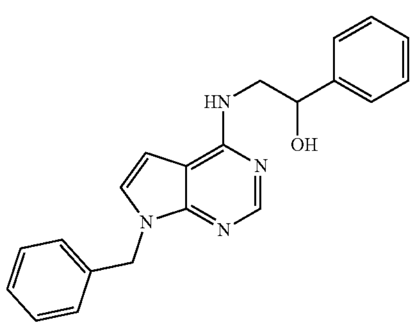 [SMILES: OC(CNc1ncnc2c1ccn2Cc1ccccc1)c1ccccc1] | 2-(7-Benzyl-7H-pyrrolo[2,3-d]pyrimidin-4-ylamino)-1-phenyl-ethanol | 9.84 (bs, 1H), 8.34 (s, 1H), 7.56 (d, 1H), 7.50 (d, 2H), 7.39-7.23 (m, 9H), 7.12 (bs, 1H), 5.46 (s, 2H), 4.91 (t, 1H), 3.74 (bs, 2H) | 195-197 | Ic |

-continued

| Expl No | Structure | AutoNom Name | NMR Assign | Melting point (C. °) | Method |
|---|---|---|---|---|---|
| 31 | 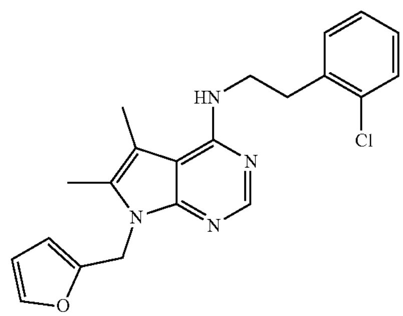 [SMILES: Cc1c(C)n(Cc2ccco2)c2ncnc(NCCc3ccccc3Cl)c12] | [2-(2-Chloro-phenyl)-ethyl]-(7-furan-2-ylmethyl-5,6-dimethyl-7H-pyrrolo[2,3-d]pyrimidin-4-yl)-amine | 8.10 (s, 1H), 7.53 (d, 1H), 7.42 (m, 1H), 7.34 (m, 1H), 7.25 (m, 2H), 6.43 (t, 1H), 6.36 (dd, 1H), 6.23 (d, 1H), 5.30 (s, 2H), 3.73 (q, 2H), 3.05 (t, 2H), 2.26 (s, 6H) | 128.9-129.2 | Ic |
| 32 | 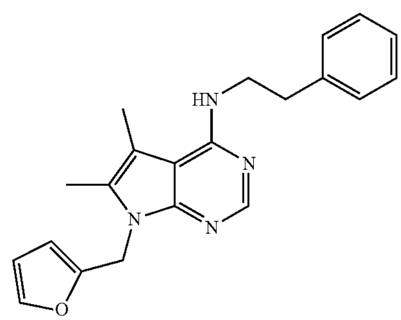 [SMILES: Cc1c(C)n(Cc2ccco2)c2ncnc(NCCc3ccccc3)c12] | (7-Furan-2-ylmethyl-5,6-dimethyl-7H-pyrrolo[2,3-d]pyrimidin-4-yl)-phenethyl-amine | 8.29 (s, 1H), 8.00 (bs, 1H), 7.57 (s, 1H), 7.36-7.21 (m, 5H), 6.40 (m, 2H), 5.45 (s, 2H), 3.84 (q, 2H), 2.97 (t, 2H), 2.33 (s, 3H), 2, 31 (s, 3H) | 221-223 | Ic |
| 33 | 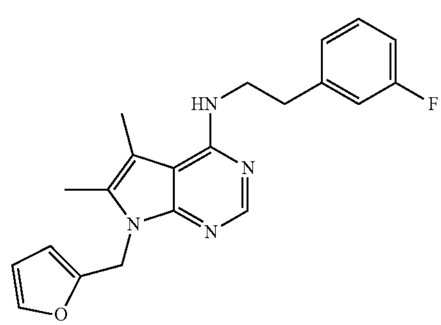 [SMILES: Cc1c(C)n(Cc2ccco2)c2ncnc(NCCc3cccc(F)c3)c12] | [2-(3-Fluoro-phenyl)-ethyl]-(7-furan-2-ylmethyl-5,6-dimethyl-7H-pyrrolo[2,3-d]pyrimidin-4-yl)-amine | 8.11 (s, 1H), 7.53 (s, 1H), 7.33 (dd, 1H), 7.10-6.99 (m, 3H), 6.37 (m, 2H), 6.23 (d, 1H), 5.30 (s, 2H), 3.70 (q, 2H), 2.94 (t, 2H), 2.26 (s, 3H), 2.25 (s, 3H) | 89-90 | Ic |
| 35 | 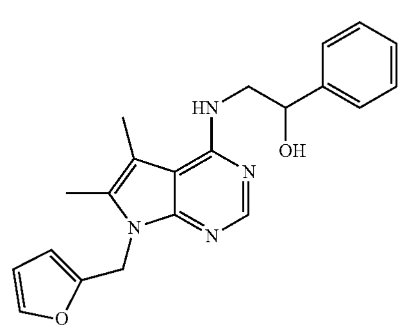 [SMILES: Cc1c(C)n(Cc2ccco2)c2ncnc(NCC(O)c3ccccc3)c12] | 2-(7-Furan-2-ylmethyl-5,6-dimethyl-7H-pyrrolo[2,3-d]pyrimidin-4-ylamino)-1-phenyl-ethanol | 8.10 (s, 1H), 7.53 d, 1H), 7.42-7.31 (m, 4H), 7.25 (m, 1H), 6.36 (m, 1H), 6.22 (m, 2H), 5.77 (bs, 1H), 5.31 (s, 2H), 4.86 (t, 1H), 3.77 (m, 1H), 3.52 (m, 1H), 2.27 (s, 3H), 2.26 (s, 3H) | 167.5-168 | Ic |

-continued

| Expl No | Structure | AutoNom Name | NMR Assign | Melting point (C. °) | Method |
|---|---|---|---|---|---|
| 36 | 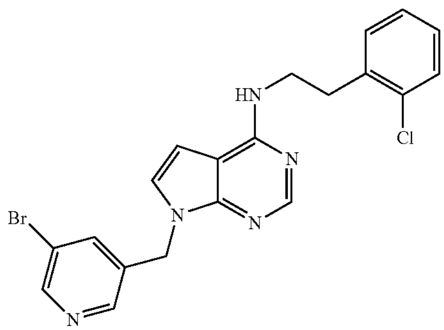 [SMILES: Clc1ccccc1CCNc1ncnc2c1ccn2Cc1cncc(Br)c1] | [7-(5-Bromo-pyridin-3-ylmethyl)-7H-pyrrolo[2,3-d]pyrimidin-4-yl]-[2-(2-chloro-phenyl)-ethyl]-amine | 8.60 (d, 1H), 8.48 (s, 1H), 8.18 (s, 1H), 7.88 (s, 1H), 7.68 (t, 1H), 7.24-7.44 (m, 5H), 6.60 (d, 1H), 5.39 (s, 2H), 3.71 (q, 2H), 3.05 (t, 2H) | 114-115 | Ic |
| 37 | 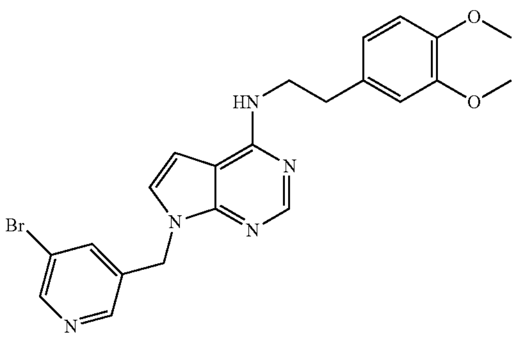 [SMILES: COc1ccc(CCNc2ncnc3c2ccn3Cc2cncc(Br)c2)cc1OC] | [7-(5-Bromo-pyridin-3-ylmethyl)-7H-pyrrolo[2,3-d]pyrimidin-4-yl]-[2-(3,4-dimethoxy-phenyl)-ethyl]-amine | 13.7-13.91 (bs, 1H), 9.69 (s, 1H), 8.64 (d, 1H), 8.51 (s, 1H), 8.33 (s, 1H), 7.95 (s, 1H), 7.61 (s, 1H), 7.04 (d, 1H), 6.96 (s, 1H), 6.83 (q, 1H), 5.51 (s, 2H), 3.78 (m, 2H), 3.69 (s, 6H), 2.91 (t, 2H) | 119-120.4 | Ic, V |
| 38 | 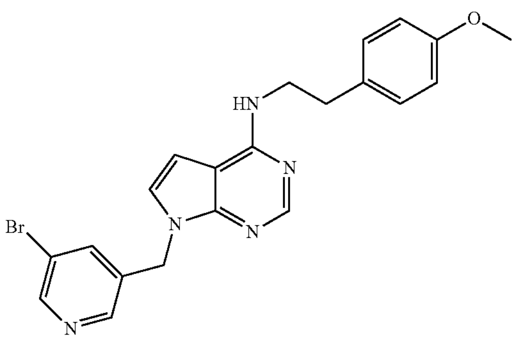 [SMILES: COc1ccc(CCNc2ncnc3c2ccn3Cc2cncc(Br)c2)cc1] | [7-(5-Bromo-pyridin-3-ylmethyl)-7H-pyrrolo[2,3-d]pyrimidin-4-yl]-[2-(4-methoxy-phenyl)-ethyl]-amine | 8.60 (d, 1H), 8.48 (d, 1H), 8.18 (s, 1H), 7.88 (s, 1H), 7.6 (t, 1H), 7.28 (d, 1H), 7.17 (d, 2H), 6.85 (d, 2H), 6.6 (d, 1H), 5.39 (s, 2H), 3.71 (s, 3H), 3.64 (q, 2H), 2.84 (t, 2H) | 100.4-100.7 | Ic |
| 39 | 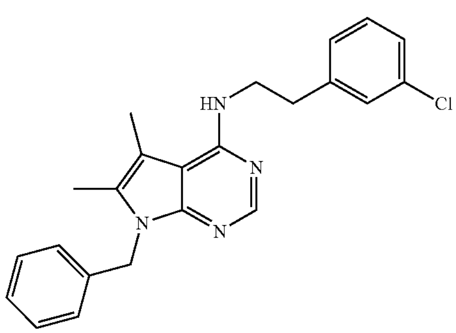 [SMILES: Cc1c(C)n(Cc2ccccc2)c2ncnc(NCCc3cccc(Cl)c3)c12] | (7-Benzyl-5,6-dimethyl-7H-pyrrolo[2,3-d]pyrimidin-4-yl)-[2-(3-chloro-phenyl)-ethyl]-amine | 8.29 (s, 1H), 8.02 (bs, 1H), 7.06 (s, 1H), 7.31 (m, 6H), 7.07 (d, 2H), 3.86 (q, 2H), 3.00 (bs, 2H), 2.50 (s, 3H), 2.33 (s, 3H) | 205-207 | Ic |

-continued

| Expl No | Structure | AutoNom Name | NMR Assign | Melting point (C. °) | Method |
|---|---|---|---|---|---|
| 40 | 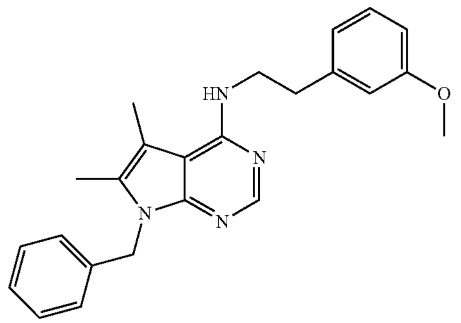 [SMILES: COc1cccc(CCNc2ncnc3c2c(C)c(C)n3Cc2ccccc2)c1] | (7-Benzyl-5,6-dimethyl-7H-pyrrolo[2,3-d]pyrimidin-4-yl)-[2-(3-methoxy-phenyl)-ethyl]-amine | 8.28 (d, 1H), 7.98 (bs, 1H), 7.27 (m, 5H), 7.07 (m, 2H), 6.87 (m, 2H), 3.79 (m, 2H), 3.72 (s, 3H), 2.92 (m, 2H), 2.34 (s, 3H), 2.07 (s, 3H) | 185-187.2 | Ic |
| 41 | 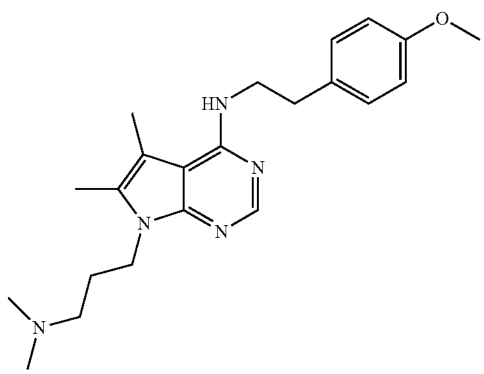 | [7-(3-Dimethylamino-propyl)-5,6-dimethyl-7H-pyrrolo[2,3-d]pyrimidin-4-yl]-[2-(4-methoxy-phenyl)-ethyl]-amine | 10.70 (br. s, 1H), 8.25 (s, 1H), 7.95 (br. s, 1H), 7.26 (dm, J = 8.5 Hz, 2H), 6.87 (dm, J = 8.5 Hz, 2H), 4.26 (t, J = 7.2 Hz, 2H), 3.80 (q, J ~ 7.0 Hz, 2H), 3.72 (s, 3H), 3.03 (m, 2H), 2.90 (t, J ~ 7.0 Hz, 2H), 2.70 (d, J ~ 3.5 Hz, 6H), 2.35 (s, 3H) | >250 | Ib, V |
| 42 | 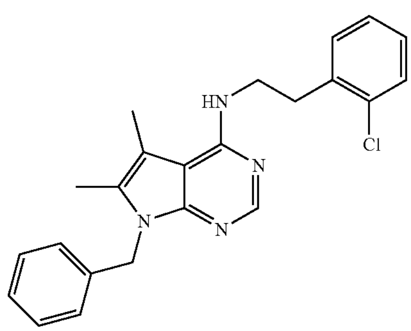 [SMILES: Cc1c(C)n(Cc2ccccc2)c2ncnc(NCCc3ccccc3Cl)c12] | (7-Benzyl-5,6-dimethyl-7H-pyrrolo[2,3-d]pyrimidin-4-yl)-[2-(2-chloro-phenyl)-ethyl]-amine | 8.29 (s, 1H), 7.95 (bs, 1H), 7.49 (m, 1H), 7.43 (m, 1H), 7.34 (m, 5H), 7.27 (bs, 2H), 5.46 (s, 2H), 3.90 (q, 2H), 3.13 (t, 2H), 2.29 (s, 3H), 2.20 (s, 3H) | 223-227 | Ic |
| 43 | 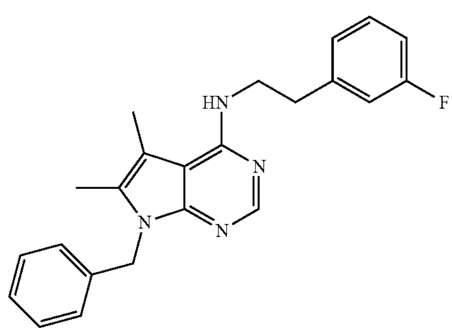 [SMILES: Cc1c(C)n(Cc2ccccc2)c2ncnc(NCCc3cccc(F)c3)c12] | (7-Benzyl-5,6-dimethyl-7H-pyrrolo[2,3-d]pyrimidin-4-yl)-[2-(3-fluoro-phenyl)-ethyl]-amine | 8.30 (s, 1H), 8.05 (bs, 1H), 7.38-7.18 (m, 6H), 7.17 (d, 1H), 7.14 (d, 2H), 5.46 (s, 2H), 3.86 (q, 2H), 3.01 (t, 2H), 2.32 (s, 3H), 2.20 (s, 3H) | 237.6-240 | Ic |

| Expl No | Structure | AutoNom Name | NMR Assign | Melting point (C. °) | Method |
|---|---|---|---|---|---|
| 44 | 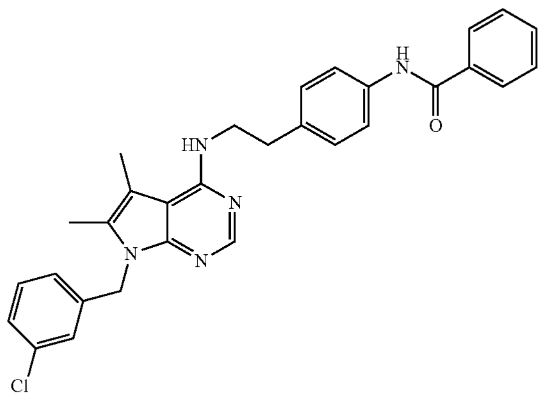 [SMILES: Cc1c(C)n(Cc2cccc(Cl)c2)c2ncnc(NCCc3ccc(NC(=O)c4ccccc4)cc3)c12] | N-(4-{2-[7-(3-Chloro-benzyl)-5,6-dimethyl-7H-pyrrolo[2,3-d]pyrimidin-4-ylamino]-ethyl}-phenyl)-benzamide | 10.18 (s, 1H), 8, 12 (s, 1H), 7.95 (d, 2H), 7.72 (d, 2H), 7.56 (m, 3H), 7.33 (m, 2H), 7.26 (d, 2H), 7.11 (s, 1H), 6.96 (d, 1H), 6.43 (t, 1H), 5.35 (s, 2H), 3.70 (q, 2H), 2.92 (t, 2H), 2.29 (s, 3H), 2.15 (s, 3H) | 151-152.3 | IIa |
| 45 | 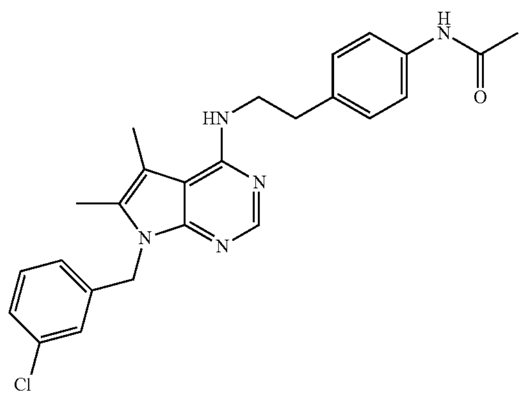 [SMILES: CC(=O)Nc1ccc(CCNc2ncnc3c2c(C)c(C)n3Cc2cccc(Cl)c2)cc1] | N-(4-{2-[7-(3-Chloro-benzyl)-5,6-dimethyl-7H-pyrrolo[2,3-d]pyrimidin-4-ylamino]-ethyl}-phenyl)-acetamide | 9.85 (bs, 1H), 8.11 (s, 1H), 7.51 (d, 2H), 7.31 (m, 2H), 7.18 (d, 2H), 7.11 (d, 1H), 6.97 (t, 1H), 6.40 (t, 1H), 5.35 (s, 2H), 3.68 (q, 2H), 2.87 (t, 2H), 2.27 (s, 3H), 2.14 (s, 3H), 2.02 (s, 3H) | 186.1-187.2 | IIa |
| 46 | 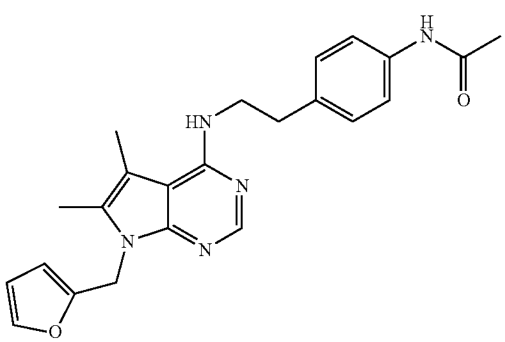 [SMILES: CC(=O)Nc1ccc(CCNc2ncnc3c2c(C)c(C)n3Cc2ccco2)cc1] | N-{4-[2-(7-Furan-2-ylmethyl-5,6-dimethyl-7H-pyrrolo[2,3-d]pyrimidin-4-ylamino)-ethyl]-phenyl}-acetamide | 9.88 (bs, 1H), 8.10 (s, 1H), 7.52 (s, 1H), 7.00 (d, 2H), 7.16 (d, 2H), 6.36 (d., 1H), 6.33 (t, 1H), 6.23 (d, 1H) 5.30 (s, 2H), 3.66 (q, 2H), 2.85 (t, 2H), 2.26 (s, 3H), 2.02 (s, 3H) | 206.8-208.1 | IIa |
| 47 | 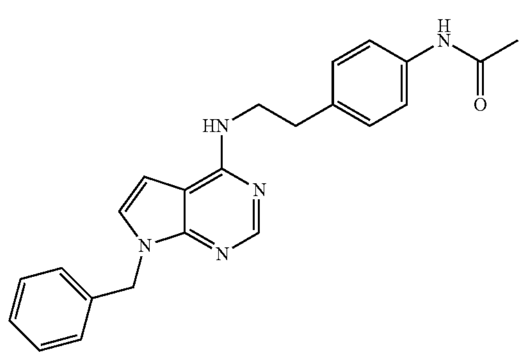 [SMILES: CC(=O)Nc1ccc(CCNc2ncnc3c2ccn3Cc2ccccc2)cc1] | N-{4-[2-(7-Benzyl-7H-pyrrolo[2,3-d]pyrimidin-4-ylamino)-ethyl]-phenyl}-acetamide | 9.84 (bs, 1H), 8.16 (s, 1H), 7.57 (t, 1H), 7.48 (d, 2H), 7.33-7.16 (m, 8H), 6.58 (d, 1H), 5.33 (s, 2H), 3.65 (q, 2H), 2.85 (t, 2H), 2.01 (s, 3H) | 228-229.5 | IIa |

| Expl No | Structure | AutoNom Name | NMR Assign | Melting point (C. °) | Method |
|---|---|---|---|---|---|
| 48 | 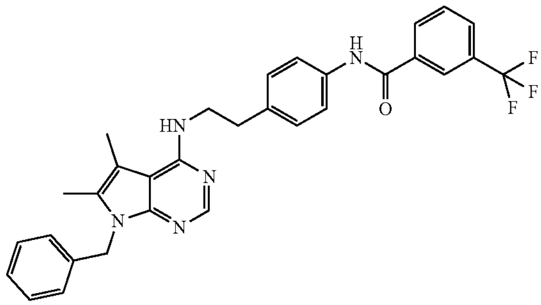 [SMILES: Cc1c(C)n(Cc2ccccc2)c2ncnc(NCCc3ccc(NC(=O)c4cccc(C(F)(F)F)c4)cc3)c12] | N-{4-[2-(7-Benzyl-5,6-dimethyl-7H-pyrrolo[2,3-d]pyrimidin-4-ylamino)-ethyl]-phenyl}-3-trifluoromethyl-benzamide | 10.42 (bs, 1H), 8.29 (s, 1H), 8.27 (d, 1H), 8.11 (s, 1H), 7.96 (d, 1H), 7.78 (t, 1H), 7.71 (d, 2H), 7.25 (m, 5H), 7.04 (d, 2H), 6.40 (t, 1H), 5.34 (s, 2H), 3.72 (q, 2H), 2.91 (t, 2H), 2.29 (s, 3H), 2.14 (s, 3H) | 110-113 | IIa |
| 49 | 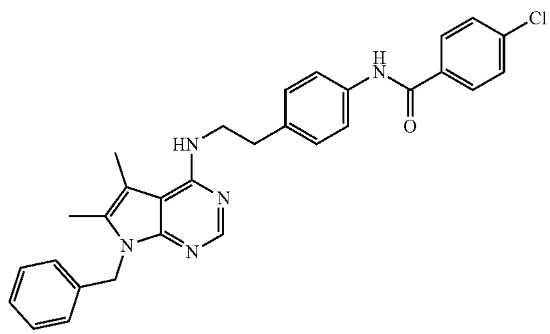 [SMILES: Cc1c(C)n(Cc2ccccc2)c2ncnc(NCCc3ccc(NC(=O)c4ccc(Cl)cc4)cc3)c12] | N-{4-[2-(7-Benzyl-5,6-dimethyl-7H-pyrrolo[2,3-d]pyrimidin-4-ylamino)-ethyl]-phenyl}-4-chloro-benzamide | 10.28 (bs, 1H), 8.11 (s, 1H), 7.98 (d, 2H), 7.70 (d, 2H), 7.60 (d, 2H), 7.27 (m, 5H), 7.03 (d, 2H), 6.40 (t, 1H), 5.34 (s, 2H), 3.70 (q, 2H), 2.91 (t, 2H), 2.28 (s, 3H), 2.14 (s, 3H) | >270 | IIa |
| 50 | 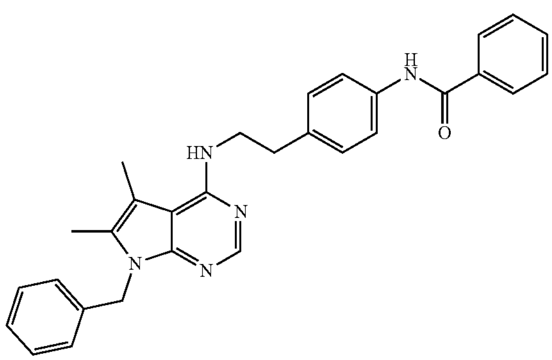 [SMILES: Cc1c(C)n(Cc2ccccc2)c2ncnc(NCCc3ccc(NC(=O)c4ccccc4)cc3)c12] | N-{4-[2-(7-Benzyl-5,6-dimethyl-7H-pyrrolo[2,3-d]pyrimidin-4-ylamino)-ethyl]-phenyl}-benzamide | 10.189 (s, 1H), 8.11 (s, 1H), 7.95 (d, 2H), 7.71 (d, 2H), 7.55 (m, 3H), 7.27 (m, 5H), 7.03 (d, 2H), 6.3 (t, 1H), 5.34 (s, 2H), 3.70 (q, 2H), 2.91 (t, 2H), 2.29 (s, 3H), 2, 14 (s, 3H) | 180-182 | IIa |
| 51 | 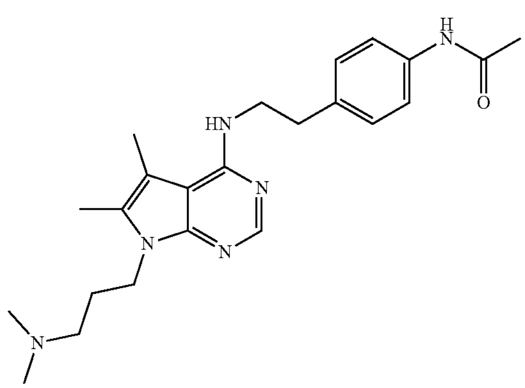 [SMILES: CC(=O)Nc1ccc(CCNc2ncnc3c2c(C)c(C)n3CCCN(C)C)cc1] | N-(4-{2-[7-(3-Dimethylamino-propyl)-5,6-dimethyl-7H-pyrrolo[2,3-d]pyrimidin-4-ylamino]-ethyl}-phenyl)-acetamide | 10.70 (bs, 1H), 9.96 (s, 1H), 8.24 (s, 1H), 7.51 (d, 2H), 7.25 (d, 2H), 4.25 (t, 2H), 3.82 (q, 2H), 3.01 (bs, 2H), 2.91 (t, 2H), 2.70 (s, 6H), 2.34 (s, 6H), 2.07 (m, 2H), 2.02 (s, 3H) | 132.7-133.7 | IIa |

-continued

| Expl No | Structure | AutoNom Name | NMR Assign | Melting point (C. °) | Method |
|---------|-----------|--------------|------------|----------------------|--------|
| 52 | 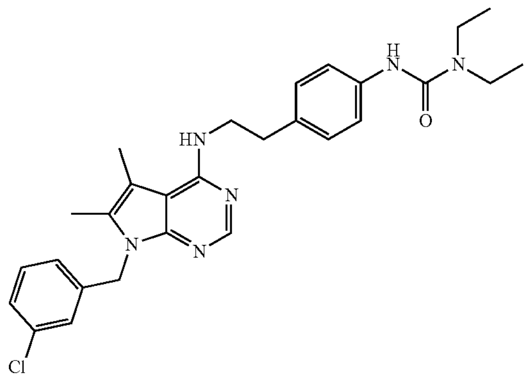 [SMILES: CCN(CC)C(=O)Nc1ccc(CCNc2ncnc3c2c(C)c(C)n3Cc2cccc(Cl)c2)cc1] | 3-(4-{2-[7-(3-Chloro-benzyl)-5,6-dimethyl-7H-pyrrolo[2,3-d]pyrimidin-4-ylamino]-ethyl}-phenyl)-1,1-diethyl-urea | 8.11 (s, 1H), 8.05 (s, 1H), 7.40 (d, 2H), 7, 31 (m, 2H), 7.31 (m, 3H), 7.12 (d, 1H), 6.38 (t, 1H), 5.35 (s, 2H), 3.67 (bs, 2H), 3.32 (m, 4H), 2.85 (t, 2H), 2.28 (s, 3H), 2.14 (s, 3H), 1.08 (t, 6H) | 112.9-113.3 | IIa |
| 53 | 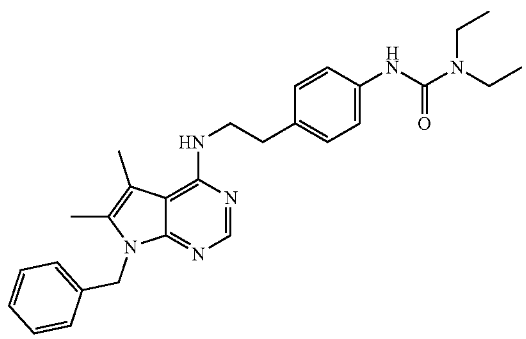 [SMILES: CCN(CC)C(=O)Nc1ccc(CCNc2ncnc3c2c(C)c(C)n3Cc2ccccc2)cc1] | 3-{4-[2-(7-Benzyl-5,6-dimethyl-7H-pyrrolo[2,3-d]pyrimidin-4-ylamino)-ethyl]-phenyl}-1,1-diethyl-urea | 8.10 (s, 1H), 8.05 (s, 1H), 7.41 (dm, J = 7.5 Hz, 2H), 7.16-7.36 (ovl. m, 3H), 7.12 (dm, J = 7.5 Hz, 2H), 7.03 (dm, J = 7.0 Hz, 2H), 6.35 (t, J ~ 6 Hz, 1H), 5.34 (s, 2H), 3.67 (q, J ~ 7.0 Hz, 2H), 3.31 (q, J = 6.8 Hz, 4H), 2.85 (t, J ~ 7.0 Hz, 2H) | 138.5-139 | IIa |
| 54 | 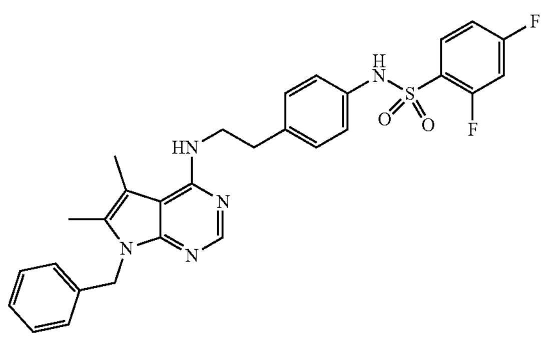 [SMILES: Cc1c(C)n(Cc2ccccc2)c2ncnc(NCCc3ccc(NS(=O)(=O)c4ccc(F)cc4F)cc3)c12] | N-{4-[2-(7-Benzyl-5,6-dimethyl-7H-pyrrolo[2,3-d]pyrimidin-4-ylamino)-ethyl]-phenyl}-2,4-difluoro-benzenesulfonamide | 10.73 (bs, 1H), 8.07 (s, 1H), 7.64 (bs, 1H), 7.25 (m, 5H), 7.15 (d, 2H), 7.05 (m, 4H), 6.31 (bs, 1H), 5.33 (s, 2H), 3.61 (q, 2H), 2.82 (t, 2H), 2.20 (s, 3H), 2.13 (s, 3H) | 183-185 | IIb |
| 55 | 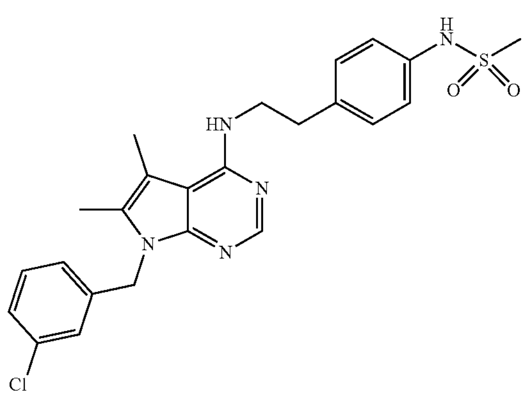 [SMILES: Cc1c(C)n(Cc2cccc(Cl)c2)c2ncnc(NCCc3ccc(NS(C)(=O)=O)cc3)c12] | N-(4-{2-[7-(3-Chloro-benzyl)-5,6-dimethyl-7H-pyrrolo[2,3-d]pyrimidin-4-ylamino]-ethyl}-phenyl)-methanesulfonamide | 9.60 (bs, 1H), 8.10 (s, 1H), 7.31 (m, 2H), 7.23 (d, 2H), 7.16 (d, 2H), 7.10 (s, 1H), 6.96 (d, 1H), 6, 42 (t, 1H) 5.35 (s, 2H), 3.69 (q, 2H), 2.93 (t, 2H), 2.89 (t, 2H), 2.27 (s, 3H), 2.14 (s, 3H) | 125-129 | IIb |

-continued

| Expl No | Structure | AutoNom Name | NMR Assign | Melting point (C. °) | Method |
|---|---|---|---|---|---|
| 56 | 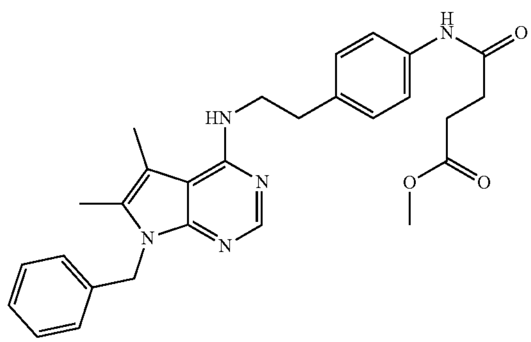 [SMILES: COC(=O)CCC(=O)Nc1ccc(CCNc2ncnc3c2c(C)c(C)n3Cc2ccccc2)cc1] | N-{4-[2-(7-Benzyl-5,6-dimethyl-7H-pyrrolo[2,3-d]pyrimidin-4-ylamino)-ethyl]-phenyl}-succinamic acid methyl ester | 9.98 (s, 1H), 8.28 (s, 1H), 7.82 (bs, 1H), 7, 51 (d, 2H), 7.26 (m, 5H), 7.07 (d, 2H), 5.46 (s, 2H), 3.79 (m, 2H), 3.59 (s, 3H), 2.93 (m, 2H), 2.33 (s, 3H), 2.20 (s, 3H) | 30-131.9 | Ic |
| 57 | 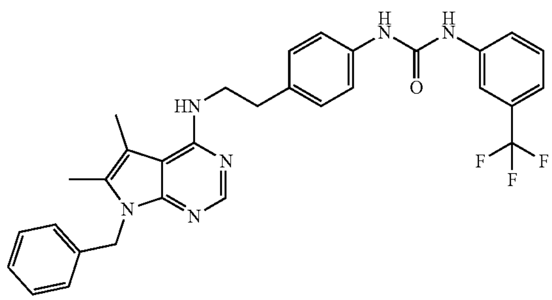 [SMILES: Cc1c(C)n(Cc2ccccc2)c2ncnc(NCCc3ccc(NC(=O)Nc4cccc(C(F)(F)F)c4)cc3)c12] | 1-{4-[2-(7-Benzyl-5,6-dimethyl-7H-pyrrolo[2,3-d]pyrimidin-4-ylamino)-ethyl]-phenyl}-3-(3-trifluoromethyl-phenyl)-urea | 9.00 (s, 1H), 8.71 (s, 1H), 8.11 (s, 1H), 8.01 (s, 1H), 7.53 (m, 2H), 7.41 (d, 2H), 7.31-7.18 (m, 6H), 7.04 (d, 2H), 6.37 (t, 1H), 5.34 (s, 2H), 3.69 (q, 2H), 2.88 (t, 2H), 2.28 (s, 3H), 2.14 (s, 3H) | 161.9-162.9 | IId |
| 58 | 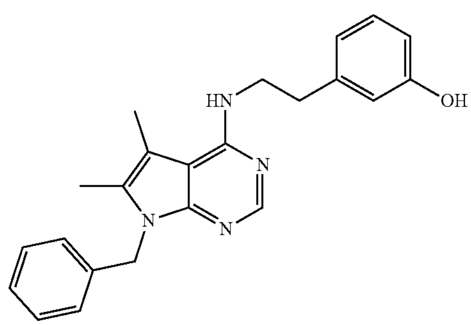 [SMILES: Cc1c(C)n(Cc2ccccc2)c2ncnc(NCCc3cccc(O)c3)c12] | 3-[2-(7-Benzyl-5,6-dimethyl-7H-pyrrolo[2,3-d]pyrimidin-4-ylamino)-ethyl]-phenol | 9.29 (bs, 1H), 8.11 (s, 1H), 7.28 (m, 3H), 7.06 (m, 3H), 6.68 (bs, 2H), 6.60 (m, 1H), 6.35 (s, 1H), 5.34 (s, 2H), 3.66 (m, 2H), 2.83 (bs, 2H), 2.27 (s, H), 2.13 (s, 3H) | 208.7-209.2 | III |
| 59 | 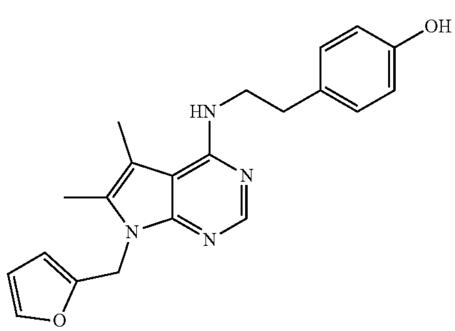 [SMILES: Cc1c(C)n(Cc2ccco2)c2ncnc(NCCc3ccc(O)cc3)c12] | 4-[2-(7-Furan-2-ylmethyl-5,6-dimethyl-7H-pyrrolo[2,3-d]pyrimidin-4-ylamino)-ethyl]-phenol | 9.15 (s, 1H), 8.11 (s, 1H), 7.53 (d, 1H), 7.05 (d, 2H), 6.69 (d, 2H), 6.50 (bs, 1H), 6.36 (dd, 1H), 6.24 (d, 1H), 5.31 (s, 2H), 3.62 (q, 2H), 2.78 (t, 2H), 2.26 (s, 3H), 2.25 (s, 3H) | 165-167 | III |

-continued

| Expl No | Structure | AutoNom Name | NMR Assign | Melting point (C. °) | Method |
|---|---|---|---|---|---|
| 60 | 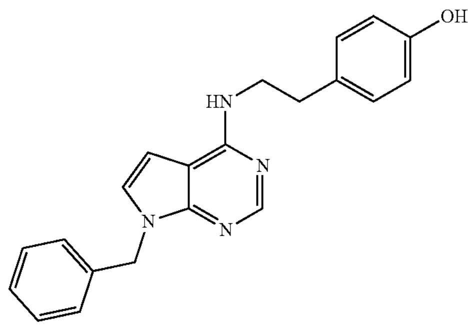 [SMILES: Oc1ccc(CCNc2ncnc3c2ccn3Cc2ccccc2)cc1] | 4-[2-(7-Benzyl-7H-pyrrolo[2,3-d]pyrimidin-4-ylamino)-ethyl]-phenol | 9.59 (bs, 1H), 9.21 (bs, 1H), 7.58 (d, 1H), 7.36-7.23 (m, 5H), 7.10 (d, 2H), 6.98 (d, 1H), 6.70 (d, 2H), 5.46 (s, 2H), 3.69 (q, 2H), 2.87 (t, 2H), | 199.2-200.6 | III |
| 61 | 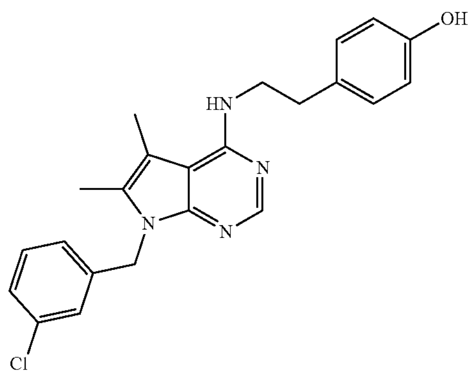 [SMILES: Cc1c(C)n(Cc2cccc(Cl)c2)c2ncnc(NCCc3ccc(O)cc3)c12] | 4-{2-[7-(3-Chloro-benzyl)-5,6-dimethyl-7H-pyrrolo[2,3-d]pyrimidin-4-ylamino]-ethyl}-phenol | 8.10 (s, 1H), 7.32 (m, 2H), 7.10 (s, 1H), 7.05 (d, 2H), 6.95 (d, 1H), 6.70 (d, 2H), 6.36 (t, 1H), 5.34 (s, 2H), 3.64 (q, 2H), 2.80 (t, 2H), 2.27 (s, 3H), 2.14 (s, 3H) | 167.7-170 | III |
| 62 | 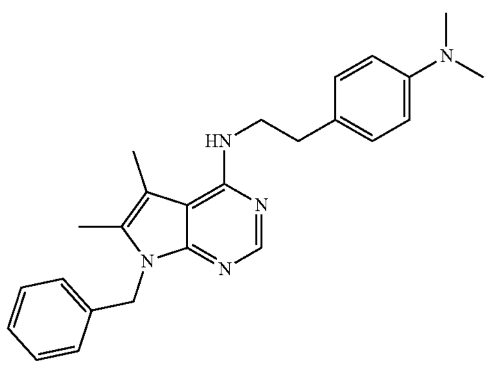 [SMILES: Cc1c(C)n(Cc2ccccc2)c2ncnc(NCCc3ccc(N(C)C)cc3)c12] | (7-Benzyl-5,6-dimethyl-7H-pyrrolo[2,3-d]pyrimidin-4-yl)-[2-(4-dimethylamino-phenyl)-ethyl]-amine | 8.10 (s, 1H), 7.25 (m, 3H), 7.09 (d, 2H), 7.03 (d, 2H), 6.68 (d, 2H), 6.29 (t, 1H), 5.34 (s, 2H), 3.64 (q, 2H), 2.85 (s, 6H), 2.80 (t, 2H), 2.27 (s, 3H), 2.13 (s, 3H) | 95-96.6 | IV |

LCMS Data of the Prepared Compounds:

| Expl No | Formula | MW | LCMS % | R. Time | M+ | M− |
|---|---|---|---|---|---|---|
| 1 | $C_{23}H_{25}N_5$ | 371.211 | 97.83 | 2.60 | 372.29 | |
| 2 | $C_{24}H_{26}N_4O$ | 386.211 | 98.41 | 3.44 | 387.36 | |
| 3 | $C_{25}H_{27}N_5O$ | 413.222 | 100 | 2.97 | 414.33 | |
| 4 | $C_{23}H_{24}N_4O$ | 372.195 | 99.2 | 3.07 | 373.31 | |
| 5 | $C_{24}H_{27}N_5O_2S$ | 449.189 | 96.63 | 3.12, 3.51 | 450.37 | |
| 6 | $C_{31}H_{27}N_5O_2$ | 501.216 | 94.28 | 3.45, 3.57 | 502.36 | |
| 7 | $C_{30}H_{28}F_2N_6O$ | 526.229 | 100 | 3.75 | 527.41 | |
| 8 | $C_{21}H_{21}N_5$ | 343.18 | 90.16 | 2.25, 2.75 | 344.27 | |
| 9 | $C_{23}H_{24}ClN_5$ | 405.172 | 98.23 | 2.82 | 406.25 | |
| 10 | $C_{21}H_{23}N_5O$ | 361.19 | 99.19 | 2.30 | 362.26 | |
| 11 | $C_{20}H_{19}BrN_6$ | 422.085 | 98.38 | 1.98 | 423.11 | |
| 12 | $C_{21}H_{30}N_6$ | 366.253 | 98.07 | 1.30, 1.42 | 367.39 | |
| 13 | $C_{22}H_{22}N_4O$ | 358.179 | 98.95 | 3.16 | 359.35 | |
| 14 | $C_{21}H_{29}N_5$ | 351.242 | 96.38 | 2.19, 2.44 | 352.35 | |
| 15 | $C_{23}H_{33}N_5O_2$ | 411.263 | 92.34 | 2.00 | 412.38 | |
| 16 | $C_{21}H_{28}ClN_5$ | 385.203 | 98.53 | 2.36 | 386.28 | |
| 17 | $C_{21}H_{28}FN_5$ | 369.233 | 96.57 | 2.17, 2.26 | 370.3 | |
| 18 | $C_{21}H_{29}N_5O$ | 367.237 | 98.88 | 1.73, 1.94 | 368.34 | |
| 19 | $C_{23}H_{22}ClFN_4$ | 408.152 | 98.41 | 3.80 | 409.28 | |
| 20 | $C_{25}H_{27}ClN_4O_2$ | 450.182 | 97.51 | 3.51 | 451.34 | |
| 21 | $C_{23}H_{22}Cl_2N_4$ | 424.122 | 97.54 | 3.95 | 425.27 | |
| 22 | $C_{26}H_{29}ClN_4O_2$ | 464.198 | 96.01 | 3.59 | 465.33 | |
| 23 | $C_{24}H_{25}ClN_4O$ | 420.172 | 95.28 | 3.73 | 421.29 | |

-continued

| Expl No | Formula | MW | LCMS % | R. Time | M+ | M− |
|---|---|---|---|---|---|---|
| 24 | $C_{23}H_{24}N_4O_2$ | 388.19 | 97.04 | 2.99 | 389.32 | |
| 25 | $C_{21}H_{19}ClN_4$ | 362.13 | 95.73 | 3.36 | 363.23 | |
| 26 | $C_{21}H_{20}N_4$ | 328.169 | 97.77 | 3.20 | 329.27 | |
| 27 | $C_{21}H_{19}FN_4$ | 346.159 | 97.79 | 3.24 | 347.27 | |
| 29 | $C_{21}H_{20}N_4O$ | 344.164 | 98.36 | 2.91 | | 343.28 |
| 31 | $C_{21}H_{21}ClN_4O$ | 380.14 | 98.84 | 3.45 | 381.26 | |
| 32 | $C_{21}H_{22}N_4O$ | 346.179 | 99.03 | 3.29 | 347.29 | |
| 33 | $C_{21}H_{21}FN_4O$ | 364.17 | 99.06 | 3.32 | 365.32 | |
| 35 | $C_{21}H_{22}N_4O_2$ | 362.174 | 99.09 | 2.99 | 363.29 | |
| 36 | $C_{20}H_{17}BrClN_5$ | 441.036 | 97.26 | 3.09 | 442.07 | |
| 37 | $C_{22}H_{22}BrN_5O_2$ | 467.096 | 96.49 | 2.70 | 468.12 | |
| 38 | $C_{21}H_{20}BrN_5O$ | 437.085 | 98.18 | 2.86 | 438.14 | |
| 39 | $C_{23}H_{23}ClN_4$ | 390.161 | 98.33 | 3.65 | | 389.02 |
| 40 | $C_{24}H_{26}N_4O$ | 386.211 | 98.54 | 3.41 | 387.36 | |
| 41 | $C_{22}H_{31}N_5O$ | 381.253 | 100 | 2.17 | 382.29 | |
| 42 | $C_{23}H_{23}ClN_4$ | 390.161 | 99.03 | 3.60 | | 388.96 |
| 43 | $C_{23}H_{23}FN_4$ | 374.191 | 97.75 | 3.40 | 374.85 | |
| 44 | $C_{30}H_{28}ClN_5O$ | 509.198 | 99.23 | 3.73 | 510.39 | |
| 45 | $C_{25}H_{26}ClN_5O$ | 447.183 | 100 | 3.24 | 448.32 | |
| 46 | $C_{23}H_{25}N_5O_2$ | 403.201 | 100 | 2.76 | | 402.32 |
| 47 | $C_{23}H_{23}N_5O$ | 385.19 | 97.51 | 2.73, 3.06 | 386.32 | |
| 48 | $C_{31}H_{28}F_3N_5O$ | 543.225 | 97.11 | 3.90 | 544.37 | |
| 49 | $C_{30}H_{28}ClN_5O$ | 509.198 | 98.08 | 3.80 | | 508.31 |
| 50 | $C_{30}H_{29}N_5O$ | 475.237 | 94.89 | 3.53 | 476.42 | |
| 51 | $C_{23}H_{32}N_6O$ | 408.264 | 100 | 1.82 | | 407.35 |
| 52 | $C_{28}H_{33}ClN_6O$ | 504.24 | 99.25 | 3.56 | 505.43 | |
| 53 | $C_{28}H_{34}N_6O$ | 470.279 | 98.95 | 3.36, 3.68 | | 469.41 |
| 54 | $C_{29}H_{27}F_2N_5O_2S$ | 547.185 | 95.88 | 3.53 | 548.4 | |
| 55 | $C_{24}H_{26}ClN_5O_2S$ | 483.15 | 98.92 | 3.33 | 484.34 | |
| 56 | $C_{28}H_{31}N_5O_3$ | 485.243 | 99.08 | 3.10 | 486.39 | |
| 57 | $C_{31}H_{29}F_3N_6O$ | 558.235 | 98.57 | 3.93 | | 557.34 |
| 58 | $C_{23}H_{24}N_4O$ | 372.195 | 95.82 | 3.07, 3.37 | | 371.02 |
| 59 | $C_{21}H_{22}N_4O_2$ | 362.174 | 93.77 | 2.87, 3.17 | | 361.29 |
| 60 | $C_{21}H_{20}N_4O$ | 344.164 | 90.75 | 2.83, 3.11 | | 343.27 |
| 61 | $C_{23}H_{23}ClN_4O$ | 406.156 | 98.89 | 3.30 | | 405.26 |
| 62 | C25H29N5 | 399.242 | 97.44 | 2.79 | 400.35 | |

Figure 6:
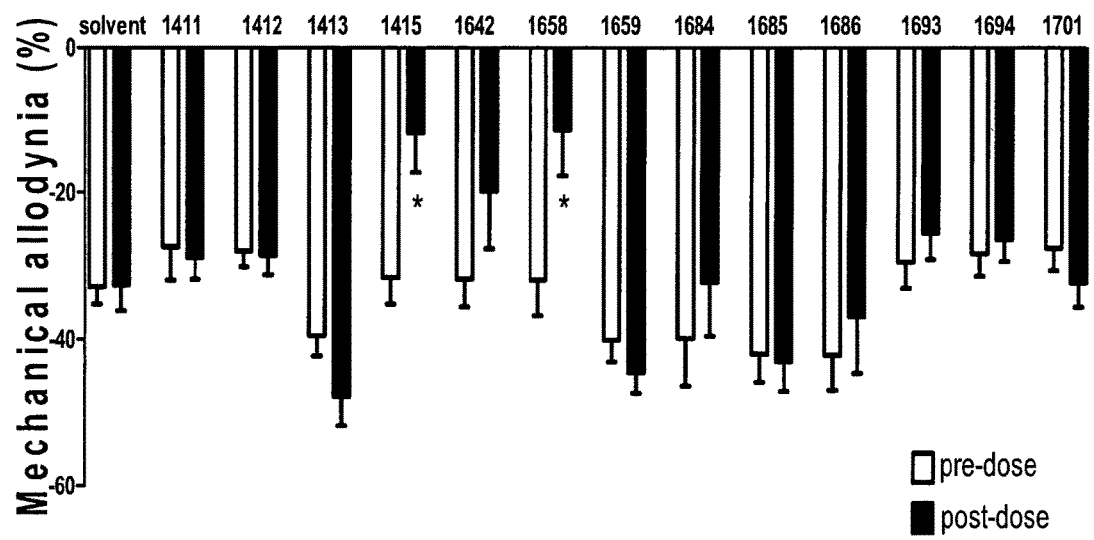

On FIG. 6 the effect of BST compounds is shown on plantar incision-evoked mechanical allodynia of the rat hindpaw. Allodynia is expressed as % change of the touch sensitivity threshold compared to the pre-operative values. Columns show the means±s.e.m. of n=8 rats in the BST compound-treated groups, and n=31 in the methylcellulose solvent-treated group; *p<0.05, vs. respective pre-dose values (Student's t-test for paired comparison).

Figure 7:
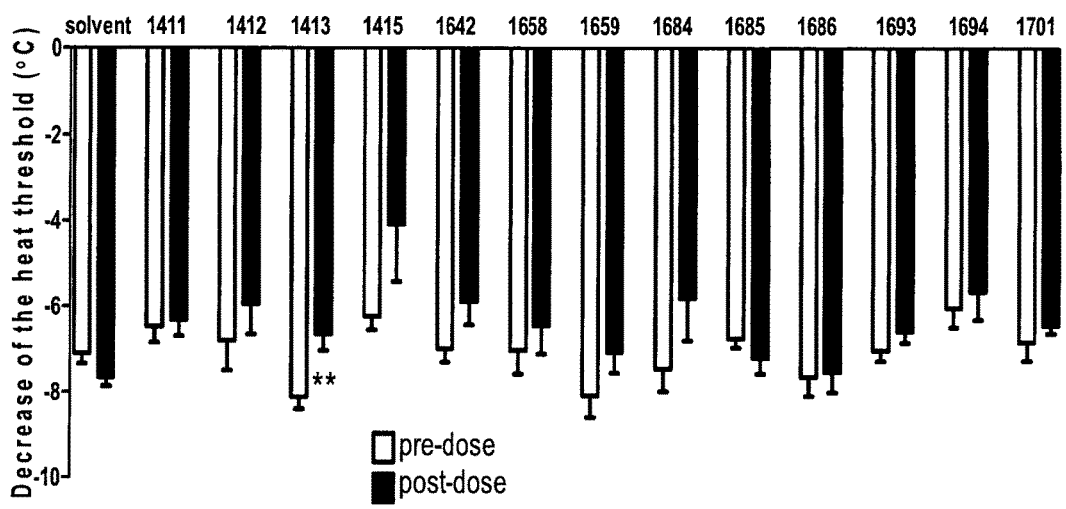

FIG. 7 shows the effect of BST compounds on plantar incision-evoked thermal allodynia of the rat hindpaw. Heat allodynia is expressed as ° C. decrease of the thermonociceptive threshold compared to the pre-operative values. Colums show the means+s.e.m. of n=8 rats in the BST compound-treated groups, and n=31 in the methylcellulose solvent-treated group; *p<0.05, vs. respective pre-dose values (Student's t-test for paired comparison).

Figure 8:
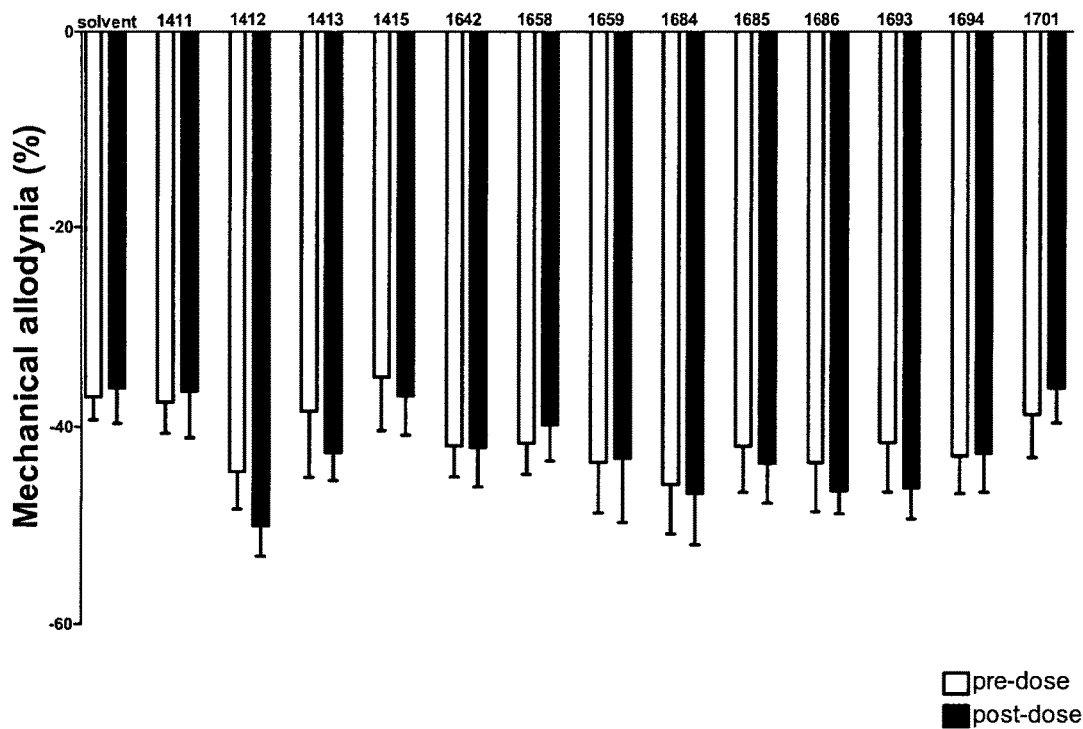

FIG. 8 shows the effect of BST compounds on sciatic nerve ligation-induced neuropathic mechanical allodynia. Allodynia is expressed as % change of the touch sensitivity threshold compared to the pre-operative values. Columns show the means+s.e.m. of n=8 rats in the BST compound-treated groups, and n=23 in the methylcellulose solvent-treated group. Neither of examined test compounds exerted significant inhibitory effect on the nerve ligation-induced mechanical allodynia (Student's t-test for paired comparison).

Figure 9:
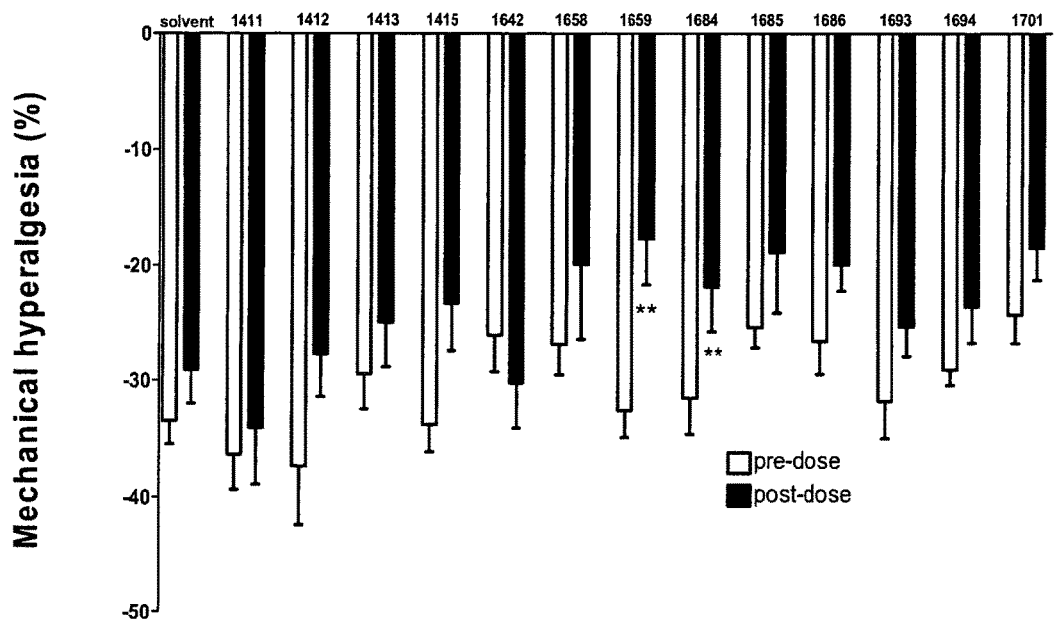

FIG. 9 displays the effect of BST compounds on plantar incision-evoked mechanical hyperalgesia of the rat hindpaw. Hyperalgesia is expressed as % change of the mechanonociceptive threshold compared to the pre-operative values. Columns show the means+s.e.m. of n=8 rats in the BST compound-treated groups, and n=23 in the methylcellulose solvent-treated group; **p<0.01, vs. respective pre-dose values (Student's t-test for paired comparison).

BIOLOGICAL EXAMPLE 1

Somatostatin $sst_4$ Receptor-Coupled G-Protein Activation Assay

Experimental Model

[$^{35}$S]GTPγS binding assay is a functional test determining agonist-induced and receptor-mediated G-protein activation which is based on the increase in guanine nucleotide exchange at G-proteins upon agonist stimulation. The interaction of a G protein-coupled receptor (GPCR) with the G protein is the first step in the transduction of the receptor binding signal to the activation of the second-messenger systems. We measured the level of [$^{35}$S]-GTPγS bound to the α subunit of G proteins and determined the efficacy of the compounds. Compounds which elicited 200% [$^{35}$S] GTPγS binding in nanomolar concentration were considered effective agonist. The examined compounds were added into the medium in 1 nM, 10 nM, 100 nM 1 μM and 10 μM concentrations.

Protocol and Investigational Technique

Membrane fractions were prepared from CHO cells stably expressing the $sst_4$ receptor in Tris-EGTA buffer (50 mM Tris-HCl, 1 mM EGTA, 3 mM $MgCl_2$, 100 mM NaCl, pH 7.4). These membrane fractions (~10 μg of protein/sample) were incubated at 30° C. for 60 min in the same Tris-EGTA buffer containing [$^{35}$S]GTPγS (0.05 nM) and increasing concentrations ($10^{-9}$ to $10^{-5}$ M) of test compounds in the presence of 30 μM GDP in a final volume of 500 μl. Non-specific binding was determined in the presence of 10

μM unlabelled GTPγS. Total binding was measured in the absence of test compounds. To calculate the specific binding, non-specific binding was subtracted from total binding. The reaction was terminated by filtrating the samples though Whatman GF/B glass fiber filters. Using 48-well Slot Blot Manifold from Cleaver Scientific filters were washed three times with ice-cold 50 mM Tris-HCl buffer (pH 7.4). After drying for 60 min at 37° C., radioactivity was measured in scintillation liquid in a Packard Tri-Carb 2800 TR scintillation counter. Test compound-induced G-protein stimulation was given as percentage over the specific [$^{35}$S]GTPγS binding observed in the absence of agonists.

Results:

Compounds which evoke 200% [$^{35}$S]GTPγS binding in nanomolar concentration are considered effective agonist. We found 5 effective compounds among the examined 13 molecules in the G-protein activation experiments. Using 100 nM concentration activation reached 245.67%, 207.67%, 210.67%, 202.67% and 194.5% in cases of BST-1411 (example 2), BST-1412 (example 41), BST-1413 (example 3), BST-1642 (example 40), and BST-1658 (example 58), respectively, therefore, these compounds can be considered as effective sst$_4$ receptor agonists.

BIOLOGICAL EXAMPLE 2

Electrical Field Stimulation-Induced Release of Calcitonin Gene-Related Peptide (CGRP) from Sensory Nerve Terminals of Isolated Rat Tracheae Experimental Model Rats were exsanguinated in deep anaesthesia (sodium thiopental, 50 mg/kg i.p.), then the whole trachea was removed and cleaned of fat and adhering connective tissues. Tracheae from two rats were placed into the same 1.8 ml organ bath to obtain sufficient amount of released peptide and perfused (1 ml/min) with pH—(7.2) controlled oxygenized Krebs solution for 60 minutes (equilibration period) at 37° C. temperature. After discontinuation of the flow, the solution was changed three times for 8 minutes to produce pre-stimulated, stimulated, post-stimulated fractions. Electrical field stimulation (40 V, 0.1 ms, 10 Hz for 120 s; 1200 pulses) was performed to elicit neurotransmitter release at the beginning of the second 8-minute period. Stimulation with 0.1 ms pulse width selectively activates very fast Na$^+$ channels which are only present in the membrane of neural structures (Birmingham and Wilson, 1963; Coburn and Tomita 1973; Szolcsányi and Barthó, 1982), therefore it excites nerve endings without influencing other excitable cells in the tracheae such as smooth muscle cells. Therefore, this in vitro system is appropriate to study the mechanism of sensory neuropeptide release and examine the effect of compounds acting directly at the sensory nerve terminals Protocol Tracheae excised from 80 male and 80 female Wistar rats (250-380 g) were used altogether in this series of studies, 50-50% females and males were used in all experimental groups. There were 14 groups: 13 for the examined compounds containing 5 experiments performed paralelly in 5 perfusion systems to provide n=5 data per group (10 tracheae per group) and a control group composed of 3 separate experiments done at the beginning, the middle and the end of the total period (n=15, 30 tracheae). The whole data set was obtained in blocks, the total study was performed on 8 experimental days during 4 weeks (2 days per week, Tuesdays and Wednesdays; two groups every occassion). Krebs solution was used in the prestimulated fraction for determining the basal CGRP outflow. During the stimulated and poststimulated fractions the incubation medium contained the examined compound in 500 nM concentration.

Investigational Technique: Measurement of CGRP Concentration by Radioimmunoassay CGRP concentration was determined from 400-400 μl samples of the organ bath solutions by means of a selective and sensitive radioimmunoassay method developed in our laboratories and described in details in several previous papers (Nemeth et al. 1998, 1999, 2006; Helyes et al., 1997, 2001, 2006; Borzsei et al., 2008). The released amount of the peptides was calculated as fmol peptide per mg wet tissue (trachea). The absolute EFS-induced CGRP outflow in each experiment was calculated by taking off the basal release measured in the first (pre-stimulated) fraction from the second and third 8-min fractions and then adding these values. The detection limits of the RIA assay was 0.2 fmol/tube.

Figure 4A:
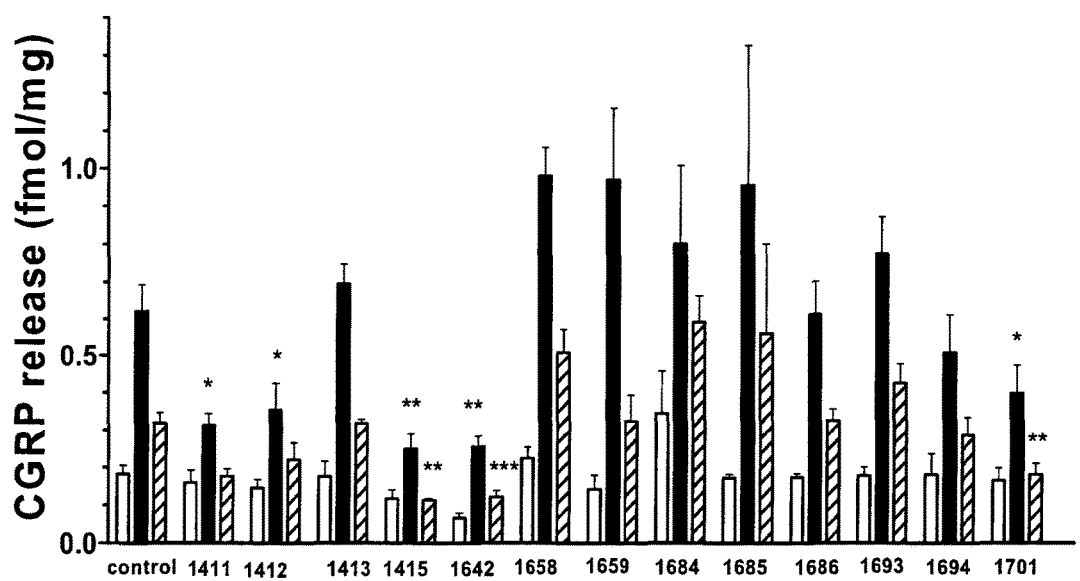
FIGS. 4A and B depict the effect of BST compounds on electrically-evoked release of CGRP from isolated rat tracheae. Each column represents the mean+s.e.m. concentration of CGRP (A) measured in the incubation medium of the prestimulated, stimulated and poststimulated 8-min fractions and the (B) absolute peptide release values calculated by substracting the basal release measured in the first, prestimulated fraction from both the stimulated and post-stimulated fractions and adding these data. In each group for compound testing n=5 experiments (5×2 tracheae), and in the control group n=15 experiments (15×2 tracheae). *P<0.05, **P<0.01 (vs. respective values of the control experiment; Student's t-test for unpaired comparison).

Results:

In the control experiments the release of CGRP increased from 0.19±0.03 fmol/mg to 0.67±0.09 fmol/mg wet tissue and 0.34±0.04 fmol/mg wet tissue, in the second and third 8-min fractions, respectively, as a result of the electrical field stimulation. The absolute release in response to this stimulation after taking off the basal release from the second and third fractions was 0.76±0.17 fmol/mg. Addition of 500 nM of 5 of the 13 examined BST compounds—BST-1411 (example 2), BST-1412 (example 41), BST-1415 (example 51), BST-1642 (example 40) and BST-1701 (example 12)—to the stimulated and post-stimulated fractions significantly inhibited the stimulation-evoked CGRP release by about 60-80%. The greatest effects of 79.55% and 72.5% inhibitions on the absolute release were obtained with BST-1415 and BST-1411, respectively (see FIGS. 4A and B).

BIOLOGICAL EXAMPLE 3

Mustard Oil-Induced Acute Neurogenic Inflammation in the Paw Skin of the Rat

Experimental Model

Figure 1:
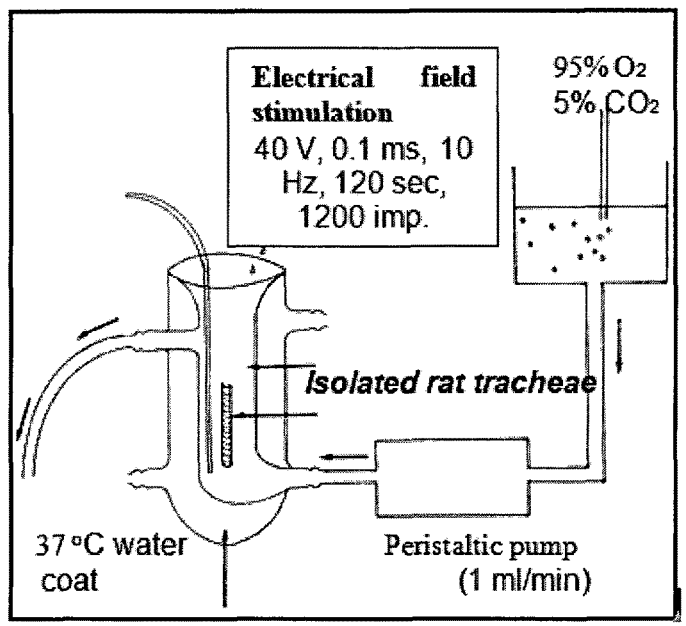
FIG. 1 shows the schematic drawing of the isolated trachea perfusion system.
Figure 2:
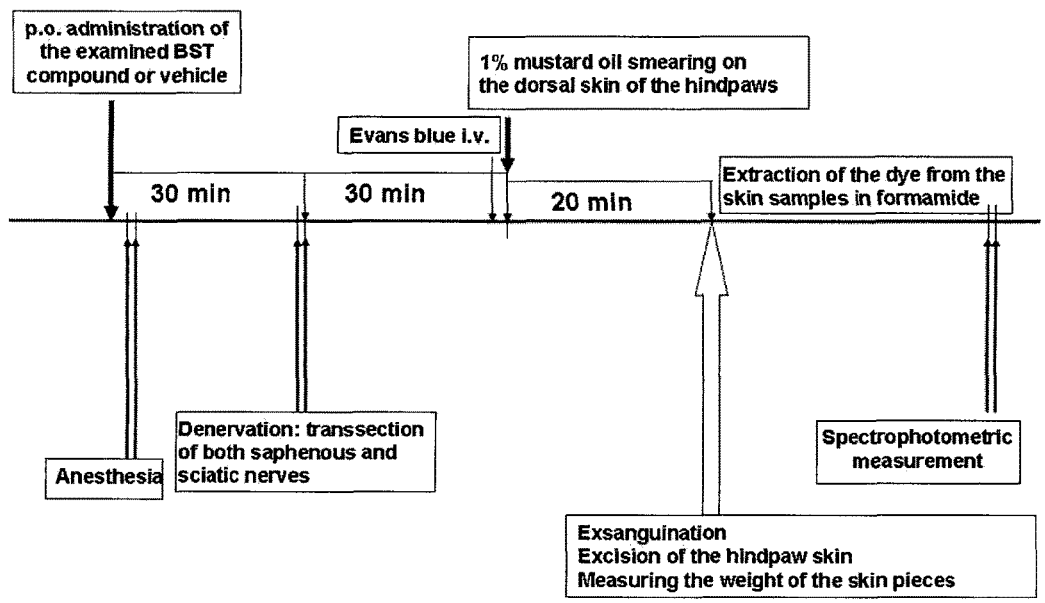
FIG. 2 depicts the schematic drawing describing the experimental protocol for the examination of acute neurogenic plasma protein leakage in the paw skin of the rat.

Deep anaesthesia was performed with sodium-thiopental (50 mg/kg i.p.). Both hindlegs of the rats were acutely denervated (the sciatic and the saphenous nerves were cut 30 min before the induction of inflammation) to avoid the influence of reflex mechanisms. Inflammation in the dorsal skin of the hindpaws was evoked by topical application of 1% mustard oil dissolved in paraffin oil. This compound selectively activates capsaicin-sensitive peptidergic fibres through the TRPA1 ion channel, therefore induces acute inflammatory reaction with exclusively neurogenic mechanisms via the release of pro-inflammatory sensory neuropeptides, such as substance P and CGRP. Extravasation of plasma albumin was measured by the Evans blue leakage method (see FIG. 2). Evans blue (50 mg/kg) which binds to plasma albumine, was injected i.v. and neurogenic inflammation was induced 5 min later. Rats were executed by exsanguination 20 min after mustard oil application. The extravasated dye in the paw skin was extracted with formamide for 72 h at room temperature for spectrophotometric determination at 620 nm. The amount of the accumulated Evans blue, which quantitatively correlates with the intensity of plasma extravasation, was expressed as μg dye/g wet skin (Helyes et at, 1997, 2001, 2006; Borzsei et al., 2008).

Protocol

One hundred and thirty four (134) Wistar rats of both sexes (70 males and 64 females; 220-350 g) kept in the Animal House of the University of Pecs in a temperature-controlled room and provided with a 12-hour light-dark cycle, standard rat chow and water ad libitum were studied in this experimental series. They were divided into 14 experimental groups: 13 for the examined compounds and one vehicle-treated control group, all of them were composed of both males and females equally. The study was undertaken in blocks with 10-14 rats per occasion, the whole data set was obtained during 14 days. The examined compound suspended in methylcellulose (100 μg/kg; 0.2 ml/100 g from the 50 μg/ml solutions) was administered p.o. 60 min before the induction of the inflammation by mustard oil smearing. Rats in the control group were treated with the same volume of the methylcellulose vehicle, there were 3-4 controls every experimental day.

Investigational Technique: Measurement of Evans Blue Accumulation in the Paw Skin Extravasation of plasma albumin in the dorsal skin of the hindpaws was measured by the Evans blue leakage method. Evans blue (50 mg/kg) which binds to plasma albumine was injected i.v. and acute neurogenic inflammation was induced 5 min later with 1% mustard oil smearing. Rats were exsanguinated 20 min after mustard oil application in deep anaesthesia. The skin of the hindpaws was removed, their weight was measured and the extravasated dye was extracted with formamide at room temperature during 72 h for photometric determination at 620 nm. The amount of the accumulated Evans blue, which quantitatively correlates with the intensity of plasma extravasation, was expressed as μg dye/g wet tissue (Szolcsányi and Barthó 1981; Helyes et al., 1997, 2001, 2006).

Figure 5:
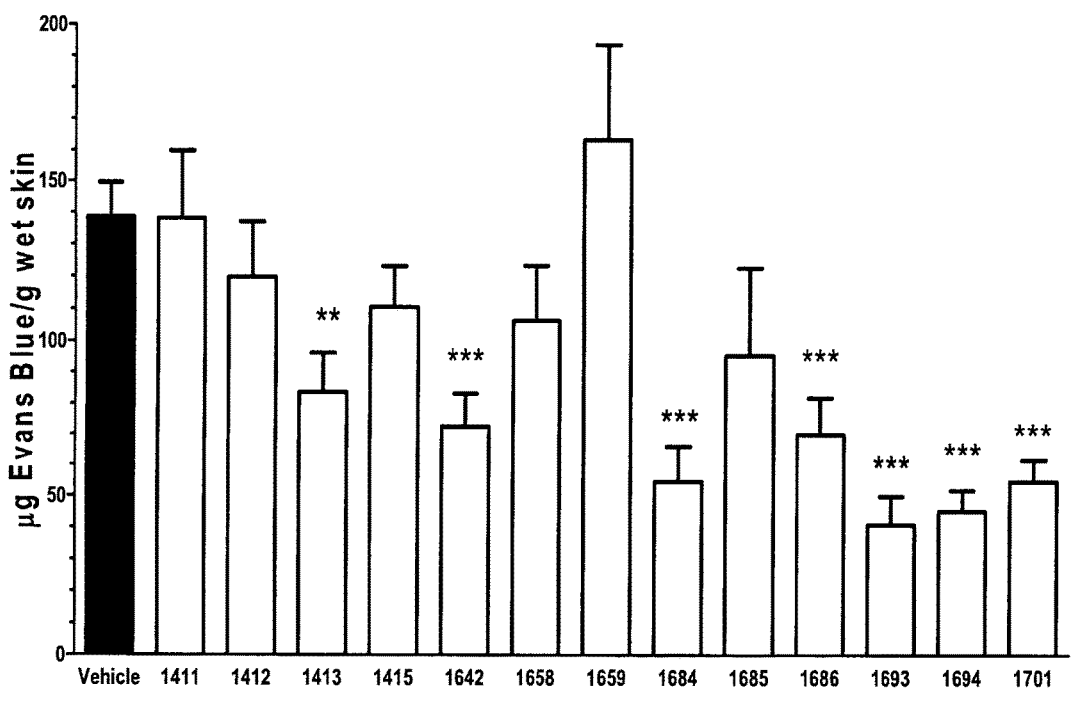
FIG. 5 illustrates the effect of BST compounds on 1% mustard oil-induced plasma protein extravasation in the acutely denervated hindpaw skin of the rat. In the control group the vehicle (MC) was applied p.o. in the same volume. Each column shows the mean±s.e.m. of n=8 rats; <0.01, *<0.001 vs. vehicle-treated control group (Student's t-test for unpaired comparison).

Results:

In control, vehicle-treated rats, topical application of 1% mustard oil induced 136.7±10.9 μg/g wet tissue Evans blue accumulation in the dorsal skin of the hindpaw within 20 min. Oral pretreatment with 100 μg/kg BST-1413 (example 3), BST-1642 (example 40), BST-1684 (example 39), BST-1686 (example 43), BST-1693 (example 1), BST-1694 (example 62), BST-1701 (example 12), significantly inhibited this acute neurogenic inflammatory response by about 40-70%, the greatest inhibitory effects of 70.4% was observed with BST-1693 (example 1)(FIG. 5).

BIOLOGICAL EXAMPLE 4

Plantar Incision-Induced Mechanical Allodynia and Thermal Hyperalgesia (Postoperative Pain Model)

Experimental Model

Rats were anaesthesized with sodium-pentobarbital (Euthasol, 40 mg/kg i.p.) and a 1 cm longitudinal incision was made through the skin, fascia and muscle of the plantar aspect of the hindpaw. Significant decrease of both the thermonociceptive and mechanonociceptive thresholds (heat and mechanical allodynia) of the paw develops 1 day after this procedure. This technique has been shown to be a reliable model to understand mechanisms of peripheral and central sensitization caused by surgery and to investigate new therapies for postoperative pain in humans (Brennan et al. 1996; Furedi et al. 2009).

Protocol

One hundred and forty five (145) female Wistar rats (150-250 g) kept in the Animal House of the University of Pecs in a temperature-controlled room provided with a 12-hour light-dark cycle, standard rat chow and water ad libitum were used in this experimental series. They were brought to the air-conditioned laboratory the day before the experiment started. Throughout the total study the same assistant handled all the animals. They were habituated to the measurement's conditions prior to the study by performing two conditioning threshold measurements, the results of which were not included in the final analysis. The observer was blind to the drug treatment of the animals. Touch sensitivity was measured with a dynamic plantar aesthesiometer (DPA) and the thermonociceptive threshold was determined with an increasing temperature water-bath (ITWB) on the same rats (see below). After conditioning, 3 control mechanonociceptive and one control thermonociceptive threshold measurements were done on 3 consecutive days prior to the incision. Rats were then anaesthesized with sodium-pentobarbital and a 1 cm longitudinal incision was made through the skin, fascia and muscle of the plantar aspect of the left hindpaw. One day after this procedure, pre-dose control measurements with both the DPA and the ITWB were performed. Test compounds were administered p.o. and post-dose touch sensitivity and thermonociceptive thresholds were measured 60 min later. The means of the 3-3 mechanonociceptive and 2-2 thermonociceptive measurements performed consecutively on both the injured (ipsilateral) and non-injured (contralateral) paws were used for analysis.

The examined compound suspended in methylcellulose (100 μg/kg; 0.2 ml/100 g from the 50 μg/ml solutions) was administered p.o. 60 min before the measurements. Rats in the control group were treated with the same volume of the methylcellulose vehicle. There were 8 rats in all the 13 test compound groups. Separate solvent-treated control groups were used for each experimental block (n=2-5), but only one contracted control group (n=31) was used for the statistical analysis after completing the study.

Figure 3:
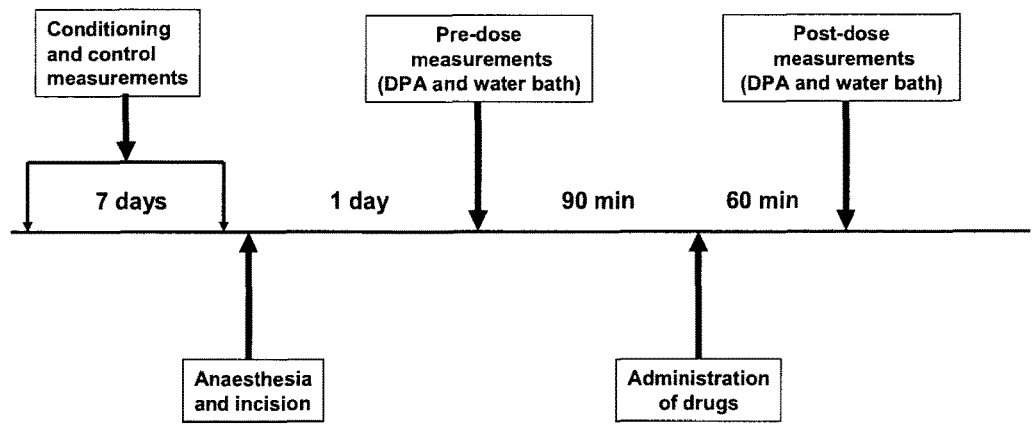
FIG. 3 depicts the schematic drawing describing the experimental protocol for the examination of plantar incision-induced hyperalgesia/allodynia.

Investigational Techniques a) Touch sensitivity of the plantar surface of the paw was measured with the Ugo Basile Dynamic Plantar Aesthesiometer (DPA; 37400, Comerio, Italy), which is an electronic von Frey device. The rats move about freely in one of the two compartments of the enclosure positioned on the metal mesh surface. Following acclimation after cessation of exploratory behaviour, the operator places the touch stimulator unit under the animal's paw, using the adjustable angled-mirror to position the filament below the target area of the paw. After pressing the "start" key an electrodynamic actuator of proprietary design lifts a straight metal filament, which touches the plantar surface and begins to exert an increasing upward force at a preset rate of application until a stop signal (when the animal removes the paw) is attained. The paw withdrawal threshold is numerically shown in grams on the digital screen (Helyes et al. 2004). Since this touch stimulus is not painful on the intact paw, its decrease after the incision expressed in percentage compared to the preoperation control values is considered to be mechanical allodynia.

b) The thermonociceptive threshold of the paw was determined with an increasing temperature water bath developed and validated in our laboratories in cooperation with Experimetria Ltd. (Budapest, Hungary). The equipment is suitable for the determination of the behavioural noxious heat threshold of rats defined as the lowest temperature at which the animal withdraws its hindpaw immersed into the water bath. The equipment consists of a tap water-filled container and a controlling unit. The cylindric plastic container (120 mm inner diameter, 140 mm height) is equipped with a built-in heating unit in its bottom that provides a homogenous and fast increase in the water temperature. The controlling unit has a 30° C. starting temperature, heating rate and a display continuously showing the actual bath temperature measured by a thermocouple at the middle position 35 mm below the water level. Heating can be interrupted by a foot switch and the corresponding bath temperature remains on the display to be recorded. After each measurement, the water bath is cooled back to the starting temperature by pumping cold water into the container controlled by a feedback mechanism while the excess water is drained through a spillway (Bölcskei et al. 2007). A starting temperature of 30° C. and a heating rate of 24° C./min was employed and the cut-off temperature was set to 53° C. Rats were lightly restrained and held in an upright position above the water bath allowing free movement of the hindlimbs. One of the hindpaws was immersed into the water and the heating process was started afterwards. At the moment when the animal withdrew its paw, heating was immediately stopped by the foot switch and the corresponding temperature was recorded as the noxious heat threshold of the examined paw. Two control threshold measurements separated by a 30 min interval were performed for the same paw of each animal and the mean of the two values was used for analysis. The significant drop of the thermonociceptive threshold after the incision is considered as heat allodynia (see FIG. 3).

Figure 4B:
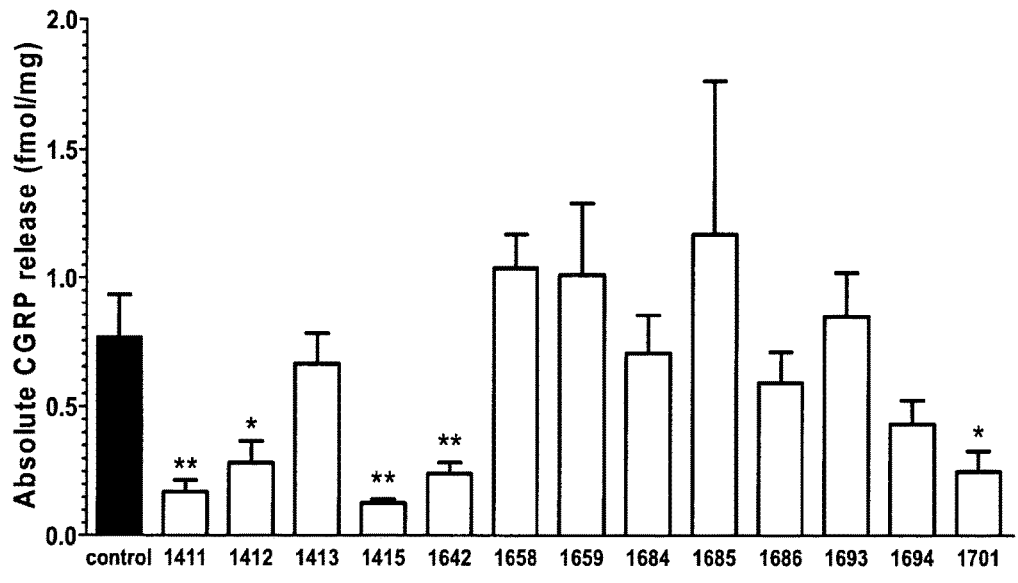

Results:

Plantar incision evoked 27.43-41.97% mechanical allodynia, which was significantly reduced by two BST compounds (BST1415 (example 51) and BST1658 (example 58)). BST1415 (example 51) caused 63%, BST1658 example 58) evoked 64.7% decrease of mechanical allodynia measured by dynamic plantar aesthesiometry (FIG. 4). Plantar incision also elicited 6-8° C. decrease of the heat threshold which effect was signicantly inhibited by BST-1413. This compound had 18.2% effectiveness (FIGS. 6 and 7).

BIOLOGICAL EXAMPLE 5

Neuropathic Mechanical Hyperalgesia and Allodynia Induced by Partial Tight Ligation of the Sciatic Nerve (Traumatic Mononeuropathy Model)

Experimental Model (Seltzer-Operation)

Wistar rats were anaesthetised with sodium-pentobarbital (Euthasol, 50 mg/kg i.p.). The common sciatic nerve was exposed unilaterally on the right side high in the thigh and ⅓-½ of the nerve trunk was carefully separated and tightly ligated using a siliconised silk suture (Ethicone 9-0). Then the wound was closed and the animals were allowed to survive for 7 days (Seltzer et al., 1990). During this period, signs of spontaneous pain (holding the legs in elevated position), mechanical hyperalgesia and allodynia developed.

Mechanonociceptive threshold of the hindpaws was measured with analgesimetry (Randall-Sellitto test) and touch sensitivity of the plantar surface with dynamic plantar aesthesiometry on the same animals. Hyperalgesia (decrease of the mechanonociceptive threshold) and allodynia (decrease of touch sensitivity) were expressed in % compared to the initial pre-operation control values. Significant decrease of the mechanonociceptive thresholds, as well as touch sensitivity thresholds developed 7 days after the surgery (Szolcsanyi et al. 2003; Sandor et al. 2006).

Protocol

One hundred and twenty seven (127) Wistar rats of both sexes (50 males and 77 females; 180-350 g) were used in the experiments. kept in the Animal House of the University of Pecs in a temperature-controlled room and provided with a 12-hour light-dark cycle, standard rat chow and water ad libitum were studied in this experimental series. They were divided into 14 experimental groups: 13 for the examined compounds and one vehicle-treated control group, all of them were composed of both males and females equally. Animals were brought to the air-conditioned laboratory the day before the study started. Throughout all the experiments the same assistant handled all the animals and they were habituated to the measurement's conditions by performing two conditioning measurements, the results of which were not included in the final analysis. The observer was blind to the drug treatment of the animals. Three control threshold measurements were made on three consecutive days prior to the nerve ligation. Seven days after the surgery pre-dose control measurements were done first with the DPA and then with the analgesimeter. Test compounds were administered p.o. and post-dose threshold measurements with both pices of equipment were performed 60 min later. Three consecutive measurements were executed on both paws and the means of these 3-3 values were used for analysis.

The examined compounds suspended in methylcellulose (100 µg/kg; 0.2 ml/100 g from the 50 µg/ml solutions) were administered p.o. Rats in the control group were treated with the same volume of the vehicle. There were 8 rats in all test compound groups. Solvent-treated control rats were investigated in every experimental block (n=2-8), but only one contracted control group (n=23) was used for the statistics. Allodynia (DPA) and hyperalgesia (Randall-Sellitto) were expressed in % values compared to the respective values before drug treatment on the same day.

Investigational Techniques a) Touch sensitivity of the plantar surface of the paw was measured with the Ugo Basile Dynamic Plantar Aesthesiometer (37400, Comerio, Italy), as described above. Since this stimulus is not painful on the intact rat paw, its decrease after the surgery is considered to be mechanical allodynia.

b) The mechanonociceptive thresholds of the hindpaw was measured with the Ugo Basile Analgesimeter (7210, Comerio, Italy; Randall-Selitto test). Continuously increasing pressure was applied on the paw of conscious rats with a cone-shaped plastic pusher. The threshold force which elicited withdrawal was read on an analog scale calibrated in grams. This pressure is slightly painful on the intact rat paw, therefore, its decrease after nerve ligation is called mechanical hyperalgesia according to the terminology of the International Association for the Study of Pain.

Results:

Partial sciatic nerve-ligation (Seltzer operation) evoked 34.91-45.79% mechanical allodynia measured by dynamic plantar aesthesiometry, which was not significantly altered by any examined BST compounds (FIG. 8). This operation also exerted 24.25-37.36% mechanical hyperalgesia measured by analgesimetry (Randall-Sellitto test), and despite the allodynia, it was significantly reduced by BST-1659 (example 4) and BST-1684 (example 39) by 46% and 31%, respectively (FIG. 9).

The invention claimed is:
1. Compounds of general formula (I) and their solvates, hydrates and pharmaceutically acceptable salts:

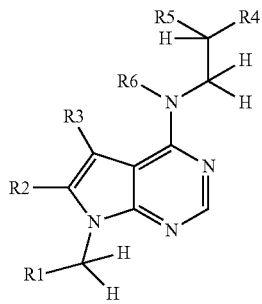

wherein
R1 is aryl or heteroaryl, which aryl or heteroaryl may be unsubstituted or substituted with a substituent or substituents other than alkoxy, or is RaRbN—(C1-4 alkyl), where Ra and Rb are independently from each other C1-4 alkyl;
R2, R3 are independently from each other hydrogen or C1-4 alkyl;
R4 is aryl optionally substituted with 1 to 3 substituent(s) selected independently from each other from the group of halogen, hydroxyl, —NH₂, —NRcRd, where Rc and Rd are independently from each other C1-4 alkyl; isoindole-1,3-dione-2-yl, —NHCOR7, —NHSO₂R7 and —NHCONHR7 or with 1 alkoxy;
R5 is hydrogen or hydroxyl;
R6 is hydrogen or C1-4 alkyl;
R7 is C1-4 alkyl, C1-4 alkyl-CO—C1-4 alkoxy, —NReRf, where Re and Rf are independently from each other C1-4 alkyl; or aryl optionally substituted with 1 to 3 substituent(s) selected independently from each other from the group of halogen, C1-4 alkyl, C1-4 alkoxy and trifluoromethyl.

2. Compounds according to claim 1, wherein
R1 is substituted or unsubstituted phenyl, furanyl, pyridinyl, thienyl or pyrimidinyl, or is RaRbN—(C1-3 alkyl), where Ra and Rb are independently from each other C1-3 alkyl;
R2, R3 are independently from each other hydrogen or C1-3 alkyl;
R4 is phenyl optionally substituted with 1 to 3 substituent(s) selected independently from each other from the group of halogen, hydroxyl, —NH₂, —NRcRd, where Rc and Rd are independently from each other C1-3 alkyl; isoindole-1,3-dione-2-yl, —NHCOR7, —NHSO₂R7 and —NHCONHR7 or with 1 alkoxy;
R5 is hydrogen or hydroxyl;
R6 is hydrogen or C1-3 alkyl;
R7 is C1-3 alkyl, C1-3 alkyl-CO—C1-3 alkoxy, —NReRf, where Re and Rf are independently from each other C1-3 alkyl, or phenyl optionally substituted with 1 to 3 substituent(s) selected independently from each other from the group of halogen, C1-3 alkyl, C1-3 alkoxy and trifluoromethyl.

3. Compounds according to claim 1, wherein
R1 is substituted or unsubstituted phenyl, furanyl, pyridinyl, thienyl or pyrimidinyl, or is RaRbN—(C1-2 alkyl), where Ra and Rb are independently from each other C1-2 alkyl;
R2, R3 are independently from each other hydrogen or C1-2 alkyl;
R4 is phenyl optionally substituted with 1 to 2 substituent(s) selected independently from each other from the group of halogen, hydroxyl, —NH₂, —NRcRd, where Rc and Rd are independently from each other C1-2 alkyl; isoindole-1,3-dione-2-yl, —NHCOR7, —NHSO₂R7 and —NHCONHR7 or with 1 alkoxy;
R5 is hydrogen or hydroxyl;
R6 is hydrogen or C1-2 alkyl;
R7 is C1-2 alkyl, C1-2 alkyl-CO—C1-2 alkoxy, —NReRf, where Re and Rf are independently from each other C1-2 alkyl; or phenyl optionally substituted with 1 to 2 substituent(s) selected independently from each other from the group of halogen, C1-2 alkyl, C1-2 alkoxy and trifluoromethyl.

4. Compounds according to claim 1, wherein
R1 is substituted or unsubstituted phenyl, furanyl or pyridinyl, is or Me₂N-ethyl;
R2, R3 are independently from each other hydrogen or methyl;
R4 is phenyl optionally substituted with 1 to 2 substituent(s) selected independently from each other from the group of halogen, hydroxyl, —NH₂, —NMe₂, isoindole-1,3-dione-2-yl, —NHCOR7, —NHSO₂R7 and —NHCONHR7 or with 1 methoxy;
R5 is hydrogen or hydroxyl;
R6 is hydrogen or methyl;
R7 is methyl, ethyl-CO-methoxy, —NEt₂, or phenyl optionally substituted with 1 to 2 substituent(s) selected independently from each other from the group of halogen, methyl, methoxy and trifluoromethyl.

5. Compounds according to claim 1, wherein
R1 is unsubstituted phenyl or furan-2-yl, 3-chloro-phenyl, 5-bromo-pyridine-3-yl or is Me₂N-ethyl;
R2, R3 are independently from each other hydrogen or methyl;
R4 is phenyl optionally substituted with 1 to 2 substituent(s) selected independently from each other from the group of halogen, hydroxyl, —NH₂, —NMe₂, isoindole-1,3-dione-2-yl, —NHCOR7, —NHSO₂R7 and —NHCONHR7 or with 1 methoxy;
R5 is hydrogen or hydroxyl;
R6 is hydrogen or methyl;
R7 is methyl, ethyl-CO-methoxy, —NEt₂, or phenyl optionally substituted with 1 to 2 substituent(s) selected independently from each other from the group of halogen, methyl, methoxy and trifluoromethyl.

6. Compounds according to claim 1, wherein
R4 is phenyl, hydroxy-phenyl, amino-phenyl, dimethyl-amino-phenyl, methoxy-phenyl, chloro-phenyl, fluoro-phenyl, (isoindole-1,3-dione-2-yl)-phenyl, phenyl-NH—C(O)—CH₃, phenyl-3-(2,4-difluoro-phenyl)-urea, phenyl-benzamide, phenyl-3-trifluoromethyl-benzamide, phenyl-4-chloro-benzamide, (N',N'-diethyl-ureido)-phenyl, phenyl-methanesulfonamide, (2,4-difluoro-benzenesulfonamidyl)-phenyl, phenyl-NH—C(O)—CH₂—CH₂—C(O)—O—CH3 or phenyl-3-(3-trifluoromethyl-phenyl)-urea.

7. Compounds according to claim 1, selected from the group consisting of
(7-Benzyl-5,6-dimethyl-7H-pyrrolo[2,3-d]pyrimidin-4-yl)-[2-(4-methoxy-phenyl)-ethyl]-amine;
[7-(3-Dimethylamino-propyl)-5,6-dimethyl-7H-pyrrolo[2,3-d]pyrimidin-4-yl]-[2-(4-methoxy-phenyl)-ethyl]-amine;

N-{4-[2-(7-Benzyl-5,6-dimethyl-7H-pyrrolo[2,3-d]pyrimidin-4-ylamino)-ethyl]-phenyl}-acetamide;
N-(4-{2-[7(3-Dimethylamino-propyl)-5,6-dimethyl-7H-pyrrolo[2,3-d]pyrimidin-4-ylamino]-ethyl}-phenyl)-acetamide;
(7-Benzyl-5,6-dimethyl-7H-pyrrolo[2,3-d]pyrimidin-4-yl)-[2-(3-methoxy-phenyl)-ethyl]-amine;
3-[2-(7-Benzyl-5,6-dimethyl-7H-pyrrolo[2,3-d]pyrimidin-4-ylamino)-ethyl]-phenol;
4-[2-(7-Benzyl-5,6-dimethyl-7H-pyrrolo[2,3-d]pyrimidin-4-ylamino)-ethyl]-phenol;
(7-Benzyl-5,6-dimethyl-7H-pyrrolo[2,3-d]pyrimidin-4-yl)-[2-(3-chloro-phenyl)-ethyl]-amine;
(7-Benzyl-5,6-dimethyl-7H-pyrrolo[2,3-d]pyrimidin-4-yl)-[2-(3-fluoro-phenyl)-ethyl]-amine;
[2-(4-Amino-phenyl)-ethyl]-(7-benzyl-5,6-dimethyl-7H-pyrrolo[2,3-d]pyrimidin-4-yl)-amine;
(7-Benzyl-5,6-dimethyl-7H-pyrrolo[2,3-d[pyrimidin-4-yl)-[2-(4-dimethylamino-phenyl)-ethyl]-amine; and
[2-(4-Amino-phenyl)-ethyl]-[7-(3-dimethylamino-propyl)-5,6-dimethyl-7H-pyrrolo[2,3-d]pyrimidin-4-yl]-amine.

8. Pharmaceutical composition comprising one or more compound(s) of general formula (I) according to claim 1 or their solvates, hydrates, pharmaceutically acceptable salts or mixtures thereof as active ingredient together with one or more pharmaceutical auxiliary material(s).

9. The compound of claim 1 which is

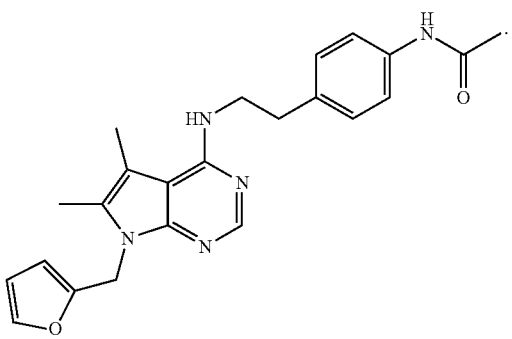 [SMILES: CC(=O)Nc1ccc(CCNc2ncnc3c2c(C)c(C)n3Cc2ccco2)cc1]

10. The compound of claim 1 wherein

R1 is aryl or heteroaryl, which aryl or heteroaryl may be optionally substituted with 1 to 3 substituent(s) selected independently from each other from the group consisting of halogen, hydroxyl, —NH$_2$, and —NRcRd, where Rc and Rd are independently from each other C1-4 alkyl; or is RaRbN—(C1-4 alkyl), where Ra and Rb are independently from each other C1-4 alkyl.

11. The compound of claim 1 wherein

R1 is aryl or heteroaryl, which aryl or heteroaryl may be optionally substituted with one substituent selected from the group consisting of halogen, hydroxyl, —NH$_2$, and —NRcRd, where Rc and Rd are independently from each other C1-4 alkyl; or is RaRbN—(C1-4 alkyl), where Ra and Rb are independently from each other C1-4 alkyl.

12. The compound of claim 1 wherein

R1 is aryl or heteroaryl, which aryl or heteroaryl may be optionally substituted with 1 to 3 halogen(s); or is RaRbN—(C1-4 alkyl), where Ra and Rb are independently from each other C1-4 alkyl.

13. The compound of claim 1 wherein

R1 is unsubstituted aryl.

14. The compound of claim 1 wherein

R1 is aryl or heteroaryl, which aryl or heteroaryl is monosubstituted with halogen.

15. The compound of claim 1 wherein

R1 is [CH$_3$—(CH$_2$)$_n$]$_2$N—CH$_2$—(CH$_2$)$_n$, where n is 0, 1 or 2.

* * * * *